(12) United States Patent
Orser et al.

(10) Patent No.: US 8,372,593 B2
(45) Date of Patent: Feb. 12, 2013

(54) METHOD FOR DETECTING MISFOLDED PROTEINS AND PRIONS

(75) Inventors: Cindy S. Orser, Lafayette, CO (US); Tao Pan, Gaithersburg, MD (US); Jasmeet Sethi, Germantown, MD (US)

(73) Assignee: Adlyfe, Inc., Rockville, MD (US)

( * ) Notice: Subject to any disclaimer, the term of this patent is extended or adjusted under 35 U.S.C. 154(b) by 1090 days.

(21) Appl. No.: 11/884,316

(22) PCT Filed: Feb. 14, 2006

(86) PCT No.: PCT/US2006/005095
§ 371 (c)(1),
(2), (4) Date: Oct. 24, 2008

(87) PCT Pub. No.: WO2006/088823
PCT Pub. Date: Aug. 24, 2006

(65) Prior Publication Data
US 2011/0081660 A1    Apr. 7, 2011

Related U.S. Application Data

(60) Provisional application No. 60/652,733, filed on Feb. 15, 2005.

(51) Int. Cl.
*G01N 33/53* (2006.01)
*G01N 31/00* (2006.01)

(52) U.S. Cl. ......... 435/7.21; 435/7.1; 436/1; 436/501; 436/518; 424/9.1; 424/520; 422/1; 422/430; 530/300; 530/350

(58) Field of Classification Search .................. None
See application file for complete search history.

(56) References Cited

U.S. PATENT DOCUMENTS

| | | | |
|---|---|---|---|
| 4,444,879 A | 4/1984 | Foster et al. | |
| 5,565,186 A | 10/1996 | Prusiner et al. | |
| 5,721,106 A | 2/1998 | Maggio et al. | |
| 5,750,361 A | 5/1998 | Prusiner et al. | |
| 5,773,572 A | 6/1998 | Fishleigh et al. | |
| 5,854,215 A | 12/1998 | Findeis et al. | |
| 5,891,641 A | 4/1999 | Prusiner et al. | |
| 5,955,343 A | 9/1999 | Holmes et al. | |
| 5,977,324 A | 11/1999 | Prusiner et al. | |
| 6,166,187 A | 12/2000 | Prusiner et al. | |
| 6,214,565 B1 | 4/2001 | Prusiner et al. | |
| 6,290,954 B1 | 9/2001 | Prusiner et al. | |
| 6,355,610 B2 | 3/2002 | Chesebro et al. | |
| 6,399,314 B1 | 6/2002 | Krishnamurthy | |
| 6,451,541 B1 | 9/2002 | Winnacker et al. | |
| 6,498,017 B2 | 12/2002 | Riesner et al. | |
| 6,534,036 B1 | 3/2003 | Collinge et al. | |
| 6,600,017 B1 | 7/2003 | Glabe et al. | |
| 6,677,125 B2 | 1/2004 | Prusiner et al. | |
| 6,750,025 B1 | 6/2004 | Hammond et al. | |
| 6,821,504 B2 | 11/2004 | Wisniewski et al. | |
| 7,125,838 B1 | 10/2006 | Stott | |
| 7,166,471 B2 | 1/2007 | Orser et al. | |
| 7,303,907 B2 | 12/2007 | Raven et al. | |
| 7,351,526 B2 | 4/2008 | Soto et al. | |
| 7,691,639 B2 | 4/2010 | Orser et al. | |
| 8,062,895 B2 | 11/2011 | Orser et al. | |
| 2001/0001061 A1 | 5/2001 | Prusiner et al. | |
| 2003/0215880 A1 | 11/2003 | Burton et al. | |
| 2004/0052928 A1 | 3/2004 | Gazit | |
| 2004/0072236 A1 | 4/2004 | Cashman et al. | |
| 2004/0224365 A1 | 11/2004 | Glabe et al. | |
| 2004/0229280 A1 | 11/2004 | Hammond et al. | |
| 2005/0026165 A1 | 2/2005 | Orser et al. | |
| 2005/0112607 A1 | 5/2005 | Bamdad et al. | |
| 2005/0118645 A1 | 6/2005 | Michelitsch et al. | |
| 2005/0181998 A1 | 8/2005 | Adessi et al. | |
| 2006/0035242 A1 | 2/2006 | Michelitsch et al. | |
| 2006/0057636 A1 | 3/2006 | Heegaard et al. | |
| 2006/0057671 A1 | 3/2006 | Orser et al. | |
| 2006/0078892 A1 | 4/2006 | Hammond et al. | |
| 2006/0178302 A1 | 8/2006 | Krafft et al. | |
| 2006/0183156 A1 | 8/2006 | Cashman et al. | |
| 2006/0188929 A1 | 8/2006 | Morel et al. | |
| 2006/0235199 A1 | 10/2006 | Mihara et al. | |
| 2006/0275910 A1 | 12/2006 | Orser et al. | |
| 2006/0286672 A1 | 12/2006 | Orser et al. | |
| 2007/0054322 A1 | 3/2007 | Gabizon | |
| 2008/0095706 A1 | 4/2008 | Orser et al. | |
| 2008/0171341 A1 | 7/2008 | Orser et al. | |
| 2009/0061462 A1 | 3/2009 | Michelitsch et al. | |

FOREIGN PATENT DOCUMENTS

| | | |
|---|---|---|
| CA | 2 443 929 A1 | 10/2002 |
| JP | 2004-155688 A | 6/2004 |
| JP | 2004-361227 A | 12/2004 |
| WO | WO 99/41279 A | 8/1999 |
| WO | WO 00/43791 A2 | 7/2000 |
| WO | WO 00/69900 A2 | 11/2000 |
| WO | WO 01/07479 | 2/2001 |
| WO | WO 01/14412 A1 | 3/2001 |
| WO | WO 01/77687 A2 | 10/2001 |
| WO | WO 02/04604 A | 1/2002 |
| WO | WO 02/053723 A3 | 7/2002 |
| WO | WO 02/097444 A | 12/2002 |

(Continued)

OTHER PUBLICATIONS

Nicotera, P., "A route for Prion Neuroinvasion", vol. 31, pp. 345-348, Aug. 16, 2001.
U.S. Appl. No. 13/176,045, filed Jul. 5, 2011, Orser et al.
Office Action issued on Sep. 13, 2011 by the Examiner in U.S. Appl. No. 11/828,953 (US 2008/0095706).
European Search Report issued on Mar. 17, 2011 in application No. EP 10188900 (corresponding to US 2008/0171341).
Extended European Search Report issued on Jul. 4, 2011 in application No. EP 10188900 (corresponding to US 2008/0171341).

(Continued)

*Primary Examiner* — Lisa Cook
(74) *Attorney, Agent, or Firm* — Foley & Lardner LLP

(57) ABSTRACT

The invention provides methods and kits for detecting conformationally altered proteins, such as prions or other proteins associated with disease states, in a sample. The methods comprise selectively capturing and separating complexes of peptide and conformationally altered protein from substances that interfere with detection of such complexes, and preferably amplification of the detection signal b addition of a second double-labeled peptide.

32 Claims, 13 Drawing Sheets

FOREIGN PATENT DOCUMENTS

WO     WO 03/001881 A2     1/2003

OTHER PUBLICATIONS

Grosset et al., "Rapid presymptomatic detection of PrP$^{sc}$ via conformationally responsive palindromic PrP peptides," Peptides, vol. 26, pp. 2193-2200, 2005.

Notice of Allowance issued on Oct. 26, 2009 by the Examiner in U.S. Appl. No. 10/494,906 (US 7,691,639).

Office Action issued on Jun. 11, 2009 by the Examiner in U.S. Appl. No. 10/494,906 (US 7,691,639).

Office Action issued on Aug. 5, 2010 by the Examiner in U.S. Appl. No. 11/979,226 (US 2008/0171341).

Office Action issued on Dec. 16, 2009 by the Examiner in U.S. Appl. No. 11/979,226 (US 2008/0171341).

Notice of Allowance issued on Apr. 6, 2011 by the Examiner in U.S. Appl. No. 11/828,953 (US 2008/0095706).

Office Action issued on Aug. 9, 2010 by the Examiner in U.S. Appl. No. 11/828,953 (US 2008/0095706).

Office Action issued on Feb. 19, 2010 by the Examiner in U.S. Appl. No. 11/828,953 (US 2008/0095706).

Fraser P E et al: "Conformation and fibfillogenesis of Alzheimer A-beta peptides with selected substitution of charged residues", Journal of Molecular Biology, London, GB, XP002957211 ISSN: 0022-2836.

Grosset et al: "Rapid presymptomatic detection of PrP<Sc> via conformationally responsive palindromic PrP peptides" Peptides, Elsevier, Amsterdam, US, vol. 26, No. 11, Nov. 2005, pp. 2193-2200, XP005137424 ISSN: 0196-9781.

Buschmann et al., "Detection of cattle-derived BSE prions using transgenic mice overexpressing bovine PrPC", Archives of Virology, Supplement 16, pp. 75-86 (2000).

Chiti, F., et al., "Designing conditions for in vitro formation of amyloid protofilaments and fibrils", Proc. Natl. Acad. Sci. USA, vol. 96, pp. 3590-3594 (1999).

Chitnumsub et al., "The Nucleation of Monomeric Parallel Beta-Sheet-Like Structures and Their Self-Assembly in Aqueous Solution", Biorganic & Medicinal Chemistry, vol. 7 (1), pp. 39-59 (1999).

Hachiya et al., Biochemical and Biophysical Research Communications, 323:339-344 (2004).

Koclsko et al., "Cell-Free Formation of Protease-Resistant Prion Protein", Nature, 370:471-474 (2004).

Lu et al., "Structural Determinants for Ligand-Receptor Conformational Selection in a Peptide G Protein-coupled Receptor", The Journal of Biological Chemistry, 282:17921-17929 (2007).

Maxson et al., "A solid-phase assay for identification of modulators of prion protein interactions", Analytical Biochemistry, 323(1): 54-64 (2003).

Nguyen, J., et al., "Prion Protein Peptides Induce -Helix to -Sheet Conformational Transitions", Biochemistry, vol. 34, pp. 4186-4192 (1995).

Pan, et al., "Conversion of alpha-helices into beta-sheets features in the formation of the scrapie prion proteins", Proc. of National Academy of Science, vol. 90, pp. 10962-10966 (1993).

Perutz, M.F., "Glutamine repeats and neurodegenerative disease: molecular aspects", TIBS, vol. 24, pp. 58-63 (1999).

Pilliot et al., "The 118-135 Peptide of Human Prion Protein Forms Amyloid Fibrils and Induces Liposome Function", J. Mol. Biol., vol. 274, pp. 381-392 (1997).

Prior, R., et al., "Selective binding of Soluble A 1-40 and A 1-42 to a Subset of Senile Plaque", Am. J. Pathology, vol. 148(6), pp. 1740-1756 (1996).

Prusiner, S.B., et al., "Prion Protein Biology", Cell 93:337-348 (1998).

Salmona, M., et al., "Molecular determinants of the physicochemical properties of a critical prion protein region comprising residues 106-126", Biochemical Journal 342:207-214 (1999).

Speed, M.A et al., "Specific aggregation of partially folded polypeptide chains: The molecular basis of inclusion body composition", Nature Biotechnology 14:1283-1287 (1996).

Speed, M.A., et al., "Polymerization Mechanism of Polypeptide Chain Aggregation", Biotechnology and Bioengineering 54(4):333-343 (1997).

Tcherkasskaya et al. "The Role of Hydrophobic Interactions in Amyloidogenesis: Example of Prion-Related Polypeptides", J. of Biomolecular Structure & Dynamics, 21(3):353-365 (2003).

Office Action dated Jan. 8, 2009, issued by the Examiner in U.S. Appl. No. 10/494,906.

Office Action dated Oct. 14, 2008, issued by the Examiner in U.S. Appl. No. 11/030,300.

Office Action issued on Apr. 16, 2012 by the Examiner in U.S. Appl. No. 11/828,953 (US 2008/0095706).

SEQUENCE LISTING

<160> NUMBER OF SEQ ID NOS: 58

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Val Ala Gly Ala Ala Ala Ala Gly Ala Val His Lys Met Asn Thr
1               5                   10                  15

Lys Pro Lys Met Lys His Val Ala Gly Ala Ala Ala Gly Ala Val
            20                  25                  30

Val

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Val Ala Gly Ala Ala Ala Ala Gly Ala Val His Lys Met Asn Thr
1               5                   10                  15

Lys Pro Lys Met Lys His Val Ala Gly Ala Ala Ala Gly Ala Val
            20                  25                  30

Val

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Val Ala Gly Ala Ala Ala Ala Gly Ala Val His Lys Met Asn Thr
1               5                   10                  15

Lys Pro Lys Met Lys His Val Ala Gly Ala Ala Ala Gly Ala Val
            20                  25                  30

Val Lys

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Pro Lys Thr Asn Met Lys His Val Ala Gly Ala Ala Ala Ala Gly
1               5                   10                  15

Ala Val Val

<210> SEQ ID NO 5
<211> LENGTH: 22

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Lys Pro Lys Thr Asn Met Lys His Val Ala Gly Ala Ala
1               5                   10                  15

Ala Ala Gly Ala Val Val
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Pro Pro Lys Pro Lys Thr Asn Met Lys His Val Ala Gly Ala Ala
1               5                   10                  15

Ala Ala Gly Ala Val Val
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Arg Lys Pro Lys Thr Asn Met Lys His Val Ala Gly Ala Ala
1               5                   10                  15

Ala Ala Gly Ala Val Val
            20

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Lys Lys Lys Pro Lys Thr Asn Met Lys His Val Ala Gly Ala Ala
1               5                   10                  15

Ala Ala Gly Ala Val Val
            20

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Pro Lys Thr Asn Met Lys His Val Ala Gly Ala Ala Ala Ala Gly
1               5                   10                  15

Ala Val Val
```

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Pro Lys Thr Asn Met Lys His Val Ala Gly Ala Ala Ala Ala Gly
1               5                   10                  15

Ala Val Val Gly Gly Gly
            20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Pro Lys Thr Asn Met Lys His Val Ala Gly Ala Ala Ala Ala Gly
1               5                   10                  15

Ala Val Val Pro Pro Pro
            20

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Pro Lys Thr Asn Met Lys His Val Ala Gly Ala Ala Ala Ala Gly
1               5                   10                  15

Ala Val Val Arg Arg Arg
            20

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Pro Lys Thr Asn Met Lys His Val Ala Gly Ala Ala Ala Ala Gly
1               5                   10                  15

Ala Val Val Lys Lys Lys
            20

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Val Ala Gly Ala Ala Ala Gly Ala Val His Lys Met Asn Thr
1               5                   10                  15

Lys Pro Lys Met Lys His Val Ala Gly Ala Ala Ala Gly Ala Val
            20                  25                  30

Val

<210> SEQ ID NO 15
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Val Val Ala Gly Ala Ala Ala Gly Ala Val His Lys
1               5                   10                  15

Met Asn Thr Lys Pro Lys Met Lys His Val Ala Gly Ala Ala Ala
            20                  25                  30

Gly Ala Val Val
        35

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Pro Pro Val Val Ala Gly Ala Ala Ala Gly Ala Val His Lys
1               5                   10                  15

Met Asn Thr Lys Pro Lys Met Lys His Val Ala Gly Ala Ala Ala
            20                  25                  30

Gly Ala Val Val
        35

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Arg Val Val Ala Gly Ala Ala Ala Gly Ala Val His Lys
1               5                   10                  15

Met Asn Thr Lys Pro Lys Met Lys His Val Ala Gly Ala Ala Ala
            20                  25                  30

Gly Ala Val Val
        35

<210> SEQ ID NO 18
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Lys Lys Val Val Ala Gly Ala Ala Ala Gly Ala Val His Lys

```
                  1               5                  10                 15
Met Asn Thr Lys Pro Lys Met Lys His Val Ala Gly Ala Ala Ala
                 20                 25                 30

Gly Ala Val Val
        35

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Val Val Asp Ala Gly Ala Ala Asp Ala Gly Ala Val His Lys
1               5                  10                 15
Met Asn Thr Lys Pro Lys Met Lys His Val Ala Gly Ala Ala Asp Ala
                 20                 25                 30

Ala Gly Ala Asp Val Val Lys
        35

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Pro Lys Thr Asn Leu Lys His Val Ala Gly Ala Ala Ala Ala Gly
1               5                  10                 15

Ala Val Val

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Lys Pro Lys Thr Asn Leu Lys His Val Ala Gly Ala Ala
1               5                  10                 15

Ala Ala Gly Ala Val Val
        20

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Pro Pro Lys Pro Lys Thr Asn Leu Lys His Val Ala Gly Ala Ala
1               5                  10                 15

Ala Ala Gly Ala Val Val
        20

<210> SEQ ID NO 23
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Arg Arg Lys Pro Lys Thr Asn Leu Lys His Val Ala Gly Ala Ala
1               5                   10                  15

Ala Ala Gly Ala Val Val
            20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Lys Lys Lys Pro Lys Thr Asn Leu Lys His Val Ala Gly Ala Ala
1               5                   10                  15

Ala Ala Gly Ala Val Val
            20

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Pro Lys Thr Asn Leu Lys His Val Ala Gly Ala Ala Ala Ala Gly
1               5                   10                  15

Ala Val Val

<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Pro Lys Thr Asn Leu Lys His Val Ala Gly Ala Ala Ala Ala Gly
1               5                   10                  15

Ala Val Val Gly Gly Gly
            20

<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Pro Lys Thr Asn Leu Lys His Val Ala Gly Ala Ala Ala Ala Gly
1               5                   10                  15

Ala Val Val Pro Pro Pro
```

```
<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Pro Lys Thr Asn Leu Lys His Val Ala Gly Ala Ala Ala Ala Gly
1               5                   10                  15

Ala Val Val Arg Arg Arg
            20

<210> SEQ ID NO 29
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Pro Lys Thr Asn Leu Lys His Val Ala Gly Ala Ala Ala Ala Gly
1               5                   10                  15

Ala Val Val Lys Lys Lys
            20

<210> SEQ ID NO 30
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Val Ala Gly Ala Ala Ala Ala Gly Ala Val His Lys Leu Asn Thr
1               5                   10                  15

Lys Pro Lys Leu Lys His Val Ala Gly Ala Ala Ala Gly Ala Val
            20                  25                  30

Val

<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Gly Val Val Ala Gly Ala Ala Ala Ala Gly Ala Val His Lys
1               5                   10                  15

Leu Asn Thr Lys Pro Lys Leu Lys His Val Ala Gly Ala Ala Ala Ala
            20                  25                  30

Gly Ala Val Val
        35

<210> SEQ ID NO 32
<211> LENGTH: 36
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 32

Pro Pro Pro Val Val Ala Gly Ala Ala Ala Gly Ala Val His Lys
1               5                   10                  15

Leu Asn Thr Lys Pro Lys Leu Lys His Val Ala Gly Ala Ala Ala Ala
            20                  25                  30

Gly Ala Val Val
        35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Arg Arg Val Val Ala Gly Ala Ala Ala Gly Ala Val His Lys
1               5                   10                  15

Leu Asn Thr Lys Pro Lys Leu Lys His Val Ala Gly Ala Ala Ala Ala
            20                  25                  30

Gly Ala Val Val
        35

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Lys Lys Val Val Ala Gly Ala Ala Ala Gly Ala Val His Lys
1               5                   10                  15

Leu Asn Thr Lys Pro Lys Leu Lys His Val Ala Gly Ala Ala Ala Ala
            20                  25                  30

Gly Ala Val Val
        35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Val Val Asp Ala Gly Ala Ala Asp Ala Ala Gly Ala Val His Lys
1               5                   10                  15

Leu Asn Thr Lys Pro Lys Leu Lys His Val Ala Gly Ala Ala Asp Ala
            20                  25                  30

Ala Gly Ala Asp Val Val Lys
        35

<210> SEQ ID NO 36
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 36

Asp Val Val Asp Ala Gly Ala Ala Asp Ala Ala Gly Ala Val His Lys
1               5                   10                  15

Met Asn Thr Lys Pro Lys Met Lys His Val Ala Gly Ala Ala Asp Ala
            20                  25                  30

Ala Gly Ala Asp Val Val
        35

<210> SEQ ID NO 37
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Val Ala Gly Ala Ala Ala Ala Gly Ala Val His Lys Met Asn Thr
1               5                   10                  15

Lys Pro Lys Met Lys His Val Ala Gly Ala Ala Ala Ala Gly Ala Val
            20                  25                  30

Val

<210> SEQ ID NO 38
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Val Val Asp Ala Gly Ala Ala Asp Ala Ala Gly Ala Val His Lys
1               5                   10                  15

Leu Asn Thr Lys Pro Lys Leu Lys His Val Ala Gly Ala Ala Asp Ala
            20                  25                  30

Ala Gly Ala Asp Val Val
        35

<210> SEQ ID NO 39
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Val Ala Gly Ala Ala Ala Ala Gly Ala Val His Lys Leu Asn Thr
1               5                   10                  15

Lys Pro Lys Leu Lys His Val Ala Gly Ala Ala Ala Ala Gly Ala Val
            20                  25                  30

Val

<210> SEQ ID NO 40
<211> LENGTH: 39
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 40

Asp Val Val Asp Ala Gly Ala Ala Asp Ala Ala Gly Ala Val His Lys
1               5                   10                  15

Met Asn Thr Lys Pro Lys Met Lys His Val Ala Gly Ala Ala Asp Ala
            20                  25                  30

Ala Gly Ala Asp Val Val Lys
        35

<210> SEQ ID NO 41
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Val Ala Gly Ala Ala Ala Ala Gly Ala Val His Lys Met Asn Thr
1               5                   10                  15

Lys Pro Lys Met Lys His Val Ala Gly Ala Ala Ala Gly Ala Val
            20                  25                  30

Val Lys

<210> SEQ ID NO 42
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Val Val Asp Ala Gly Ala Ala Asp Ala Gly Ala Val His Lys
1               5                   10                  15

Leu Asn Thr Lys Pro Lys Leu Lys His Val Ala Gly Ala Ala Asp Ala
            20                  25                  30

Ala Gly Ala Asp Val Val Lys
        35

<210> SEQ ID NO 43
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Val Ala Gly Ala Ala Ala Ala Gly Ala Val His Lys Leu Asn Thr
1               5                   10                  15

Lys Pro Lys Leu Lys His Val Ala Gly Ala Ala Ala Gly Ala Val
            20                  25                  30

Val Lys

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 44

Lys Leu Val Phe Phe Ala Glu Asp Val Gly Ser Asn Lys Gly Ala Ile
1               5                   10                  15

Ile Gly Leu Met Lys
            20

<210> SEQ ID NO 45
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Gly Lys Leu Val Phe Phe Ala Glu Asp Val Gly Ser Asn Lys
1               5                   10                  15

Gly Ala Ile Ile Gly Leu Met Lys
            20

<210> SEQ ID NO 46
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Pro Pro Pro Lys Leu Val Phe Phe Ala Glu Asp Val Gly Ser Asn Lys
1               5                   10                  15

Gly Ala Ile Ile Gly Leu Met Lys
            20

<210> SEQ ID NO 47
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Arg Arg Lys Leu Val Phe Phe Ala Glu Asp Val Gly Ser Asn Lys
1               5                   10                  15

Gly Ala Ile Ile Gly Leu Met Lys
            20

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Lys Lys Lys Leu Val Phe Phe Ala Glu Asp Val Gly Ser Asn Lys
1               5                   10                  15

Gly Ala Ile Ile Gly Leu Met Lys
            20

<210> SEQ ID NO 49
<211> LENGTH: 24
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 49

Lys Leu Val Phe Phe Ala Glu Asp Val Gly Ser Asn Lys Gly Ala Ile
1               5                   10                  15

Ile Gly Leu Met Lys Gly Gly Gly
            20

<210> SEQ ID NO 50
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Leu Val Phe Phe Ala Glu Asp Val Gly Ser Asn Lys Gly Ala Ile
1               5                   10                  15

Ile Gly Leu Met Lys Pro Pro Pro
            20

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Leu Val Phe Phe Ala Glu Asp Val Gly Ser Asn Lys Gly Ala Ile
1               5                   10                  15

Ile Gly Leu Met Lys Arg Arg Arg
            20

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Leu Val Phe Phe Ala Glu Asp Val Gly Ser Asn Lys Gly Ala Ile
1               5                   10                  15

Ile Gly Leu Met Lys Lys Lys Lys
            20

<210> SEQ ID NO 53
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Val Ala Gly Ala Ala Ala Ala Gly Ala Val His Lys Leu Asn Thr
1               5                   10                  15

Lys Pro Lys Leu Lys His Val Ala Gly Ala Ala Ala Ala Gly Ala Val
            20                  25                  30
```

Val

<210> SEQ ID NO 54
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Val Ala Gly Ala Ala Ala Ala Gly Ala Met His Lys Met Asn Thr
1               5                   10                  15

Lys Pro Lys Met Lys His Met Ala Gly Ala Ala Ala Gly Ala Val
            20                  25                  30

Val

<210> SEQ ID NO 55
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Val Ala Gly Ala Ala Ala Ala Gly Ala Val His Lys Met Asn Thr
1               5                   10                  15

Lys Pro Lys Met Lys His Val Ala Gly Ala Ala Ala Gly Ala Val
            20                  25                  30

Val

<210> SEQ ID NO 56
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Val Val Ala Gly Ala Ala Ala Ala Gly Ala Val His Lys Leu Asn Thr
1               5                   10                  15

Lys Pro Lys Leu Lys His Val Ala Gly Ala Ala Ala Gly Ala Val
            20                  25                  30

Val Lys

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Val Ala Gly Ala Ala Ala Ala Gly Ala Met His Lys Met Asn Thr
1               5                   10                  15

Lys Pro Lys Met Lys His Met Ala Gly Ala Ala Ala Gly Ala Val
            20                  25                  30

Val Lys

```
<210> SEQ ID NO 58
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Val Val Ala Gly Ala Ala Ala Gly Ala Val His Lys Met Asn Thr
1               5                   10                  15

Lys Pro Lys Met Lys His Val Ala Gly Ala Ala Ala Gly Ala Val
            20                  25                  30

Val Lys
```

METHOD FOR DETECTING MISFOLDED PROTEINS AND PRIONS

CROSS-REFERENCE TO RELATED APPLICATIONS

The present application relies on, and claims the benefit of the filing date of, U.S. provisional patent application No. 60/652,733, filed 15 Feb. 2005, the entire disclosure of which is hereby incorporated herein by reference.

GOVERNMENT SUPPORT

The inventions disclosed herein were partly funded by grants. Therefore, to the extent that rights to such inventions may accrue to the U.S. Government, the following statement, required under 37 C.F.R. §401.14(f)(4) applies: This invention was made with government support under 5 R44 HL070399-04, awarded by the National Institute of Health. The government has certain rights in the invention.

BACKGROUND OF THE INVENTION

The invention relates to the field of detection of proteins in biological samples. More specifically, the invention relates to methods and kits for detecting proteins and prions in a sample containing biological substances, and compositions employed by those methods and kits.

Numerous diseases and disorders affecting humans and animals have been determined or postulated to involve misfolded cellular proteins. Misfolding of naturally occurring normal cellular proteins is thought to cause the protein to lose activity, or, in many cases, behave abnormally. Misfolding of normal cellular proteins often causes formation of high molecular weight deposits or plaques within affected cells. Diseases that are known or thought to be associated with such misfolding of normal cellular proteins include Alzheimer's disease (AD), in which the A beta (amyloid beta) protein is involved; cerebral amyloid angiopathy (CAA); Parkinson's Disease, in which α-synuclein deposits in Lewy bodies are involved; Pick's Disease and frontal temporal dementia, in which the tau protein is involved; Amylotrophic Lateral Sclerosis (AML), in which superoxide dismutase is involved; Huntington's Disease, in which the protein huntingtin is involved; and the numerous Transmissible Spongiform Encephalopathies (TSE), such as Creutzfeldt-Jakob disease (CJD), variant Creutzfeldt-Jakob disease (vCJD), Bovine Spongiform Encephalopathy (BSE; Mad Cow Disease), in which prion proteins are involved.

Many of the diseases and disorders associated with misfolded proteins and the associated deposits and plaques of these proteins are diseases and disorders of the central nervous system. Indeed, most of the diseases and disorders are neurodegenerative in nature, causing diminished neural cell function or neural cell death. The mechanisms by which deposits or plaques are formed from the misfolded proteins, and the relationship of deposit or plaque formation to the disease-associated neurodegenerative processes are not well-defined.

A group of proteins that are among these plaque-forming proteins are the prion proteins. Currently, prion proteins are under intense investigation due to their association with neurodegenerative diseases in farm animals and the human population, and their apparent transmission through biological materials from one animal or human to another, including apparent cross-species transmission.

It is widely held that prions, which are the infections agents of neurodegenerative diseases, are, in fact, entirely proteinaceous, and it has been postulated that the prion protein is the entity known as a prion. The prion protein is a protein referred to as PrP 27-30 or $PrP^C$. It is an approximately 28-kilodalton hydrophobic glycoprotein that, when misfolded, aggregates into rod-like filaments found as plaques or deposits in infected brains. Prions exist normally as innocuous cellular proteins. However, prions possess an innate capacity to convert their structure and cause several deadly brain diseases of the dementia type in humans and animals. The dominating hypothesis is that, unlike all other infectious pathogens, infection is caused by an abnormal conformation of the prion protein, which acts as a template and converts normal prion conformations into abnormal conformations.

Complete prion protein-encoding genes have been cloned, sequenced, and expressed in transgenic animals. $PrP^C$ is encoded by a single-copy cellular gene and is normally found at the outer surface of neurons, attached to the membrane by way of a glycolipid moiety at the C-terminal portion of the protein. Cycling of the protein from the surface to the interior is known to occur, but the function of this cycling is not yet elucidated. Through an as-yet unclear post-translational process, under certain circumstances, $PrP^{Sc}$ is formed from the normal, cellular $PrP^C$. Neurodegenerative disease then can develop, a process that can take as much as decades to become clinically evident in humans.

The delay between the time of infection and manifestation of clinical symptoms of neurodegenerative disease is cause for heightened concern because this delay can permit unknowing transmission of the disease from one individual to others. For example, it can permit an animal infected with a prion to be slaughtered, and the potentially infectious products from that animal to enter the animal or human food stream. Likewise, it can permit an infected human to transmit infectious material to others through blood or organ donation. Thus, it is of great interest to the health community, the farming industry, and the general public to monitor animals and animal products (such as meat), and to monitor medical samples derived from humans (such as blood donations and organ donations) to reduce or eliminate the likelihood of transmission of prion proteins from infected individuals to others.

The normal cellular protein ($PrP^C$) can be differentiated from the misfolded, infective protein ($PrP^{Sc}$) by numerous methods, the most common of which being susceptibility or resistance to degradation by proteases, such as Proteinase K, and detection with antibodies raised against one form of the protein or the other, or prior to or after proteinase digestion.

Many of the current techniques used to detect the presence of prion-related infections rely on gross morphological changes in the brain, or immunochemical techniques that are generally applied only after clinical symptoms are manifest, and which require biopsy material or material taken post mortem. Of course, by the time gross morphological changes in the brain are evident, a human may have transmitted infections particles to others through blood donations or donation of organs or tissues. Similarly, by the time post mortem analysis of animal tissue has been completed, products from the animal may have already entered the food stream and potentially infected other animals or even humans.

Other techniques in development or use rely on catalytic propagation of the misfolded form of cellular proteins involved in neurodegenerative diseases, such as prion protein. For example, Published U.S. Patent Application 2005/0026165 A1, which is incorporated herein in its entirety by reference, discloses the use of peptide probes to detect small amounts of misfolded protein in samples. In 2005/0026165 A1, peptides having sequences that bind to misfolded proteins are exposed to samples suspected of containing the misfolded protein. If misfolded protein is present, the probes bind to the misfolded protein. Binding causes a conformational change in the probe that permits it to bind to other probe molecules. Binding of other probe molecules to the misfolded protein-probe complex causes a conformational change in the newly bound probe, which converts it to a conformation that is capable of binding to yet another probe molecule in the mixture. The design of the probes permits a detectable signal to be generated when the target misfolded protein is present.

Although numerous techniques for detecting misfolded proteins, such as infectious prion proteins, exist in the art, there still exists a need for improved techniques that are rapid, inexpensive, reliable, reproducible, easy to use, and/or provide improved sensitivity. Improving the sensitivity relates to virtually all other needs. Furthermore, there exists a need for this technique to be convenient to carry out by means of a high-throughput kit.

SUMMARY OF THE INVENTION

The present invention addresses needs in the art, including increasing the detection sensitivity, by providing methods and kits for detection of conformationally-altered proteins, such as prions, which are associated with any number of neurodegenerative diseases and disorders. Conformationally dependent peptides, such as those that are labeled peptides designed to mimic the folding reaction of $PrP^C$ converting to $PrP^{Sc}$ (also known as, and used equivalently for, $PrP^{TSE}$), provide the basis for a highly sensitive diagnostic assay for misfolded proteins, such as $PrP^{Sc}$. Superior sensitivity is achieved due to signal amplification as additional peptides, such as labeled peptides, are recruited in a target-enriched solution to undergo a similar conformational change, enabling the effective detection of the misfolded protein, such as $PrP^{Sc}$, in the blood or other tissues of animals and humans containing the misfolded proteins, such as those infected with certain $PrP^{Sc}$-related diseases or those with Alzheimer's disease.

Among the many uses for the invention, the methods and kits can be used to screen samples from humans or animals for the presence of misfolded proteins. In addition, the methods and kits can be used for diagnostic purposes, such as to diagnose an animal or human as having a disease or disorder associated with a misfolded protein, such as a prion protein. The methods and kits can further be used to monitor the amount of misfolded protein in an individual over time. In general, the methods and kits can be used with any probe or set of probes that permits catalytic propagation of misfolded protein conformation in a sample containing a misfolded protein. Thus, the methods and kits are broadly applicable to detection of numerous diseases and disorders, particularly those of a neurodegenerative nature.

DETAILED DESCRIPTION OF EMBODIMENTS OF THE INVENTION

Figure 1:
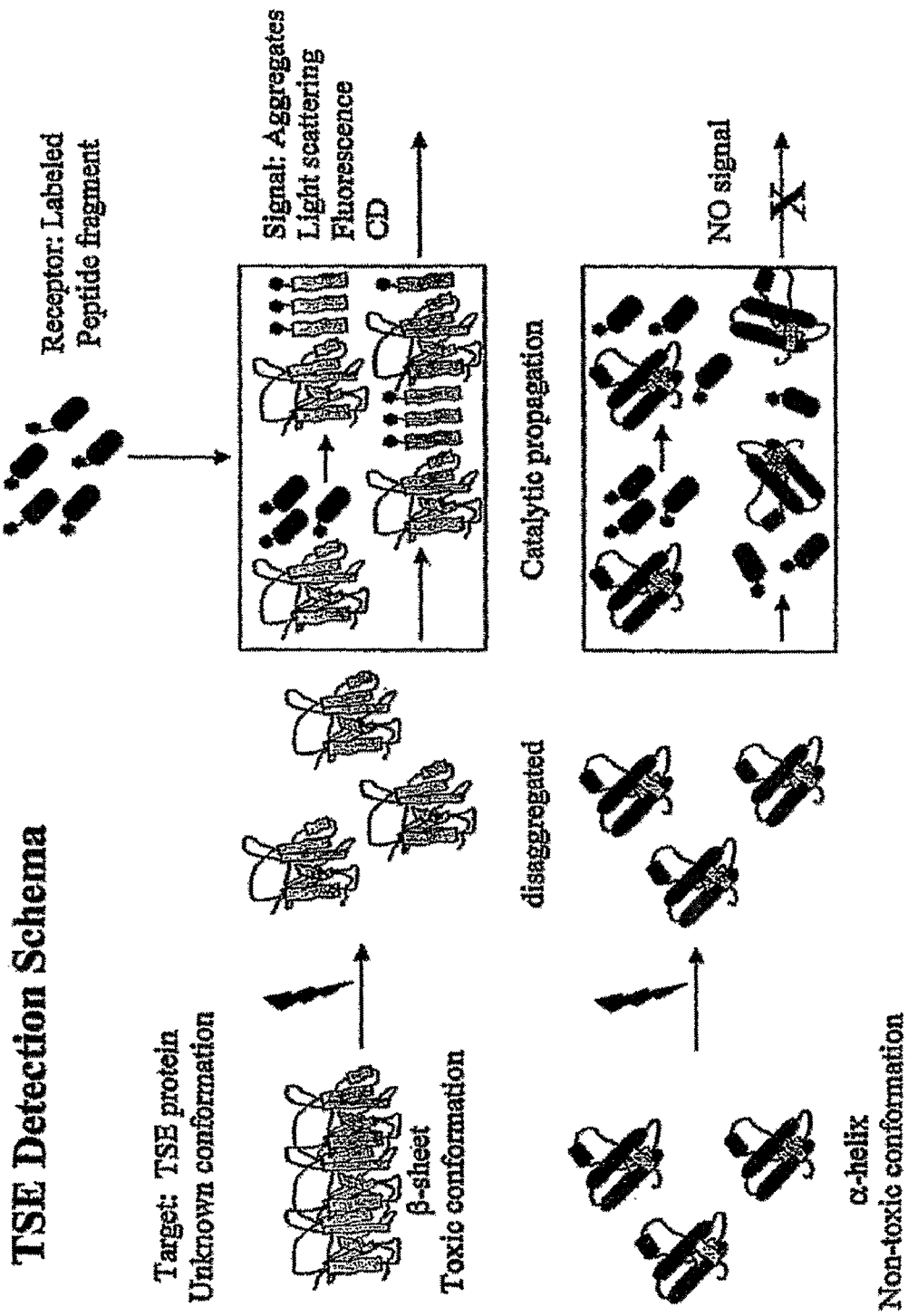
FIG. 1 depicts generally a catalytic-propagation assay used according to the invention.

The present disclosure describes methods and kits for detection of misfolded proteins in samples. Unless otherwise noted, all terms used herein have their customary meaning within the biotechnology, protein biochemistry, and medical diagnostics fields.

As used herein, and consistent with use in the scientific literature, the terms "prion" and "prion protein" are used interchangeably to indicate the proteinaceous material that causes neurodegenerative disease states in animals and humans. Prion and prion protein are used interchangeably to indicate both the normal cellular conformation of a protein and the infectious or disease-causing conformation. Where helpful for clarity, the particular form is used: $PrP^C$ for normal cellular conformation or $PrP^{Sc}$ for disease-causing conformation.

The terms "prion", "prion protein", "$PrP^{Sc}$ protein", and the like are used interchangeably herein to refer to the infectious $PrP^{Sc}$ form of a PrP protein. Particles are comprised largely, if not exclusively, of $PrP^{Sc}$ molecules encoded by a PrP gene. Prions are distinct from bacteria, viruses, and viroids. Known prions infect animals and cause Scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI). As used herein "prion" includes all forms of prions causing all or any of these diseases or others in any animals, in particular in humans and domesticated farm animals.

"Protein" refers to any polymer of two or more individual amino acids (whether or not naturally occurring) linked via a peptide bond, and occurs when the carboxyl carbon atom of the carboxylic acid group bonded to the α-carbon of one amino acid (or amino acid residue) becomes covalently bound to the amino nitrogen atom of the amino group bonded to the α-carbon of an adjacent amino acid. These peptide bond linkages, and the atoms comprising them (i.e., α-carbon atoms, carboxyl carbon atoms (and their substituent oxygen atoms), and amino nitrogen atoms (and their substituent hydrogen atoms)) form the polypeptide backbone of the protein.

The term "protein" is understood to include the terms "polypeptide" and "peptide" (which may be used interchangeably herein) within its meaning. In addition, proteins comprising multiple polypeptide subunits or other components (for example, an RNA molecule, as occurs in telomerase) will also be understood to be included within the meaning of "protein" as used herein. Similarly, fragments of proteins and polypeptides are also within the scope of the invention and may be referred to herein as "proteins".

"Conformation" refers to the presence of a particular protein conformation, for example, an α-helix, parallel and antiparallel β-strands, leucine zipper, zinc finger, etc. In addition, conformational constraints can include amino acid sequence information without additional structural information. A "conformational change" is a change from one conformation to another.

"Conformationally altered proteins" are all proteins that have a single primary amino acid sequence, but that can exist in an individual or in vitro in both a normal three-dimensional conformation and a three-dimensional conformation that is associated with a disease. The conformationally altered protein can be associated with the disease in any detectable way. For example, it can cause the disease, can be a factor in a symptom of the disease, or can be present in a biological sample or in vivo as a result of other substances that cause the disease or are a result of the disease. Conformationally altered proteins have both normal conformations and various misfolded conformations.

The exact mechanism by which the sequence of a protein encodes the proper fold is unknown. In order to achieve the native state encoded by the fold, the protein molecule must convert to a unique conformation selected from many alternatives. Functional proteins are typically soluble and can adopt a variety of structures including coils and ordered elements. Ordered elements include the α-helix predominant in proteins such as myoglobin and hemoglobin. During the human aging process, in some proteins the soluble structure (e.g., α-helical regions) becomes conformationally altered into β-sheet structures that undergo aggregation associated with loss of function.

"Conformational probes" are peptides that have amino acid sequences that are sufficiently similar to sequences present in a target misfolded protein to permit association (by any known means, such as hydrophobic interaction or van der Waals interaction) between the probe and target protein. Association of a conformational probe to a misfolded protein causes the probe (or a portion of the probe molecules present) to change conformation to a second conformation, which is different from the conformation in which it existed when exposed to the misfolded protein. Although not required, conformational probes may assume a predominantly β-sheet conformation upon association with the misfolded protein. Conformational probes can be, but are not necessarily, labeled with a detectable label, such as a fluorescent moiety.

"Labels" refer to molecules capable of detection, including radioactive isotopes, fluorescers, luminescers, chemiluminescers, enzymes, enzyme substrates, enzyme cofactors, enzyme inhibitors, chromophores, dyes, metal ions, metal sols, ligands such as biotin, and the like. The term "fluorescer" refers to a substance or a portion thereof that is capable of exhibiting fluorescence in the detectable range. Particular examples of labels that may be used with the invention include, but are not limited to fluorescein, rhodamine, dansyl, umbelliferone, Texas red, luminol, acradimum esters, NADPH, β-galactosidase, horseradish peroxidase, glucose oxidase, alkaline phosphatase and urease. The label can also be an epitope tag (e.g., a His-His tag), an antibody or a detectable oligonucleotide.

There are at least twenty proteins that are associated with human disease when they adopt a conformationally altered state. The normal wild-type form of prion protein ($PrP^C$) prefers a monomeric state, while the abnormal, disease-causing form ($PrP^{Sc}$) more readily takes on a multimeric state. The present invention, while focusing on prion detection, is equally applicable to all diseases and disorders associated with proteins that adopt a conformationally altered state.

Protein structures can be determined by a variety of experimental or computational methods, several of which are described below. Protein structure can be assessed experimentally by any method capable of producing at least low-resolution structures. Such methods currently include X-ray crystallography and nuclear magnetic resonance (NMR) spectroscopy. NMR enables determination of the solution conformation (rather than crystal structure) of biomolecules. Generally, biomolecule structures determined by NMR spectroscopy are of moderate resolution compared to those determined by crystallography. Other techniques useful in studying biomolecule structure include circular dichroism (CD), fluorescence, and ultraviolet-visible absorbance spectroscopy. See, for example, *Physical Biochemistry: Applications to Biochemistry and Molecular Biology*, Second Ed., W.H. Freeman & Co., New York, N.Y., 1982 for descriptions of these techniques. Any suitable technique can be used in accordance with the present invention.

"Equivalent" refers to amino acid sequences that are similar in sequence to the amino acid sequence of the protein to be analyzed but have at least one, but fewer than five, differences, substitutions, additions, or deletions. Thus, the substitution of one or more amino acid in a given sequence which does not substantially change the basic function of that amino acid, is equivalent for purposes of describing the present invention.

"Homology", "homologs of", "homologous", "identity", and "similarity" refer to sequence similarity between two peptides, with identity being a more strict comparison. Homology and identity can each be determined by comparing a position in each sequence which may be aligned for purposes of comparison. When a position in the compared sequence is occupied by the same amino acid, then the molecules are identical at that position. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. A "non-homologous" sequence shares less than 40% identity, though preferably less than 25% identity, with one of the sequences used in the present invention. Related sequences share more than 40% identity, preferably at least about 50% identity, more preferably at least about 70% identity, even more preferably at least about 90% identity, and most preferably at least about 99% identity.

The term "percent identical" refers to sequence identity between two amino acid sequences. Identity can each be determined by comparing a position in each sequence which may be aligned for purposes of comparison. When an equivalent position in the compared sequences is occupied by the same amino acid, then the molecules are identical at that position; when the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md.

The terms "interact" and "bind" as used herein mean detectable interactions (e.g., biochemical interactions) between molecules, such as interaction between protein-protein, protein-nucleic acid, nucleic acid-nucleic acid, and protein-small molecule or nucleic acid-small molecule in nature.

Unless otherwise indicated, the practice of the present invention will employ conventional methods of chemistry, biochemistry, molecular biology, immunology, medicine, and pharmacology, within the skill of the art. Such techniques can be understood by referring to the current the literature, such as for example *Methods in Enzymology* Vol. 278: Fluorescence Spectroscopy (L. Brand and M. L. Johnson, Eds., Academic Press, Inc., 1997); *Methods in Enzymology* Vol. 309: Amyloid, Prions and Other Protein Aggregates (R. Wetzel, Ed., Academic Press, Inc., 1999); *Handbook of Experimental Immunology*, Vols. I-IV (D. M. Weir and C. C. Blackwell, Eds., 1986, Blackwell Scientific Publications); and *Handbook of Surface and Colloidal Chemistry* (Birdi, K. S., Ed., CRC Press, 1997).

In a first aspect of the invention, methods of detecting the presence and/or amount of a misfolded protein in a sample are provided. In general, the methods comprise providing a sample containing or suspected of containing a misfolded protein, such as a prion; providing at least one conformational probe; combining the sample with the conformational probe to make a mixture; incubating the mixture for an amount of time sufficient for an association of at least one molecule of misfolded protein and at least one molecule of probe to form a complex; exposing the mixture to an environment that separates, at least partially, the complex from at least one other substance in the mixture; and detecting the presence or absence of an association between at least one probe and the misfolded protein, wherein said detecting is preferably enhanced by addition of a second conformational probe to amplify the analytical signal. Of course, in the various embodiments of the present invention, these steps may be performed in different orders to achieve the desired goals.

In accordance with the methods of the invention, providing can be any activity that results in a sample containing or suspected of containing a misfolded protein, or containing a conformational probe being present and available for use in the method. Thus, providing can comprise removal of a tissue, organ, body part, or liquid from an individual. Likewise, it can comprise obtaining a biological sample, such as blood or meat, from an individual, company, or government agency that obtained the sample. In addition, it can comprise taking a sample obtained from an individual and processing it in some way, such as to eliminate one or more biological or other substances. Although processing of the sample prior to combining it with the probe is encompassed by the invention, in some embodiments, such processing is not performed. With regard to providing of at least one conformational probe, such providing can comprise synthesizing, using any suitable technique, one or more conformational probes, obtaining one or more probes synthesized by another, and obtaining a mixture of two or more probes, or at least one probe and contaminating substances, then purifying the probe, at least to some extent, from the contaminants.

The sample can be any sample containing or suspected of containing a misfolded protein. A sample that is suspected of containing a misfolded protein can be any sample taken from any animal or human in which a disease or disorder associated with a misfolded protein exists. Thus, the level of suspicion need not be high; it is simply enough to know or suspect that the individual from whom the sample was taken was in a population at risk of suffering from one of the diseases or disorders associated with a misfolded protein. Examples of samples include, but are not limited to, blood or blood products or blood by-products; neural tissue, including, but not limited to brain tissue; meat or meat by-products; skin or skin products (including mucous membranes); intestine casings; milk; and urine.

In certain embodiments, one or more control reactions are performed in parallel with the method of detecting a misfolded protein. In these embodiments, the control reactions are considered as part of the method even though they can be, but are not necessarily, run in separate reaction containers. Control reactions can be positive controls or negative controls. Any number of controls can be run to identify and monitor the performance of any step or any component used in the method. In certain positive controls, the sample provided is known to have at least one misfolded protein, and thus is used to monitor the success and, where appropriate, sensitivity of the reaction. In certain negative controls, the sample is known not to contain a misfolded protein (e.g., distilled water or water-based buffer). Furthermore, in certain embodiments, a series of control reactions are performed to obtain a standard curve against which the sample of interest is compared. As is known in the art for other assays to detect substances in samples, control reactions can be performed before the method for detecting misfolded protein, at the same time as the method for detecting misfolded protein, or after the method for detecting misfolded protein.

The conformational probe can be any probe that satisfies the criteria set forth above. Various suitable exemplary probes are disclosed in Published U.S. Patent Application 2005/0026165 A1, which is incorporated herein in its entirety by reference. Preferable conformational probe are disclosed herein, below. The conformational probe can be provided as a single probe (i.e., a collection of identical peptides, all having the same amino acid sequence) or can comprise multiple different probes (i.e., a collection of two or more peptides having different amino acid sequences, each peptide being present in multiple copies). In preferred embodiments, the conformational probe(s) is labeled with a moiety that is detectable. Examples of detectable labels include, but are not limited to, luminescent labels, fluorescent labels, radioactive labels, and immunogenic labels.

The probes can be provided in any form, including, but not limited to, purified solutions in water, dried powders, or dispersions in aqueous or organic liquids. Thus, they can be provided in compositions comprising purified probe alone, a mixture of purified probes of different sequences, or unpurified probe or mixtures of probes with one or more non-probe substances (e.g., buffers, liquids, or detection reagents). Probes can comprise a single label or multiple labels. In certain embodiments, two or more labels are provided on each probe. For example, a probe of the invention can comprise a label attached to each end of the probe (N-terminus and C-terminus). In some embodiments, the conformational change in the probe upon associating with the target misfolded protein causes the two labels to come into close proximity, which enhances the signal generated from the probes as compared to the signals generated when the probes are not in close proximity.

According to the method, combining can be any action that causes at least a portion of the sample and at least a portion of the composition comprising the probe(s) to form a single composition. As used in the method, this single composition is referred to as a mixture; however, any single composition comprising the two components is encompassed by the terminology. Thus, combining can comprise adding a liquid composition of probe(s) to the sample or vice versa. Likewise, it can comprise adding a dried composition of probe(s) to sample or vice versa. The mixture so formed can be subjected to conditions that cause the two compositions to fully combine with each other (e.g., centrifugation, shaking, or pipetting) or the two compositions can simply be added to one another and permitted to mix through simple diffusion, dissolution, etc. It is not critical how the sample and probe(s) be combined as long as the two are permitted to contact each other such that at least one probe can contact at least one misfolded protein, if present.

The method includes incubating the probe(s) and sample for an amount of time sufficient for an association of at least one molecule of misfolded protein and at least one molecule of probe to form a complex. The time of incubation will vary based on known physical properties, such as concentration of probe(s) and/or misfolded protein, temperature, presence or absence of substances that inhibit or promote interaction of proteins and peptides, and the like. Routine experimentation can be carried out by a person of ordinary skill in the art, practicing this invention, in order to understand the impacts of various system parameters on the incubation time.

The method of the invention comprises exposing the mixture of the sample and the probe(s) to conditions that separate, at least partially, complexes of probe and misfolded protein, if present, from at least one other substance in the mixture. This separation step can be performed after the incubation step, concurrent with the incubation step, or partially concurrently with the incubation step.

In embodiments wherein incubation and separation are concurrent, certain benefits can arise. Isolation is performed as the association between the probe and target protein is occurring, thereby reducing the time required to detect the presence of misfolded protein, and eliminating steps and reagents needed to detect the presence of misfolded protein. Rapid detection of complexes of probe and target misfolded protein is possible because complexes of probe and target misfolded protein will typically be high-molecular weight entities having unique or unusual properties (typically due to the high levels of β-sheet structures present). The complexes can be isolated, at least partially, from other substances in the mixture using rapid, well-characterized techniques, such as size-exclusion chromatography or filtration.

Furthermore, incubating and separating at the same time permits high sensitivity. That is, because the mixture is separated into two or more fractions prior to detection, and the separation technique used is preferably chosen based on characteristics that remove substances that interfere with signal generation or detection, fractions containing probe-misfolded protein complexes will have signal-to-noise ratios that are improved over the original mixture. Because the fraction containing the probe-misfolded protein complex will be devoid or essentially devoid of interfering substances, the amount of signal needed to detect the presence of the complexes will be less than needed in the mixture itself.

According to the methods of the invention, the separating can be accomplished by any suitable technique. One convenient physical characteristic of complexes of probe and misfolded protein is typically their large mass. Thus, a suitable technique for separation will take advantage of the size of the complexes, and can include filtration or size-exclusion chromatography. Other physical characteristics that can be taken advantage of will be apparent to those of skill in the art, and can include solubility or hydrophobicity under various conditions, or affinity to a particular stationary phase, for example. In some embodiments, separating can comprise binding of the probe, target polypeptide, or complex to a solid support, such as a magnetic bead, and relying, at least in part, on the properties of the solid support to achieve separation.

The methods of the invention include detecting the presence of probes associated with misfolded proteins. Detecting can be accomplished by any means known in the art for detecting protein-protein interactions. In some embodiments, the probes are labeled, and detection is by way of detecting a signal generated by a probe associated with a misfolded protein. In some embodiments, the probe includes two signal-generating moieties whose signals are enhanced when brought into close proximity. In these embodiments, the amino acid sequences of the probes are designed such that binding of the probes to a misfolded protein brings the two signal-generating moieties into close proximity.

The invention generally includes peptides that interact preferentially with pathogenic forms of a misfolded protein. In certain embodiments, the peptides described herein interact preferentially with pathogenic forms of a prion as compared to non-pathogenic forms of the prion. Using preferred embodiments of this invention, high sensitivities can be achieved. Examples of suitable peptides that achieve high sensitivities include those described herein. In certain embodiments, peptides interact preferentially with $PrP^{Sc}$ as compared to $PrP^C$. The peptides may be specific for $PrP^{Sc}$ from a single species or from multiple species.

In preferred embodiments, one or more end-labeled peptides of the invention are added to capture the pathogenic prion by forming a complex between the peptide(s) and the pathogenic misfolded protein or prion. This complex is then enriched in the sample by means of a solid phase comprising one or more properties imparting a capability to separate, at least partially, the complex from at least one other component of the sample, preferably from substantially all of the rest of the sample, which is not bound to the solid phase. The solid phase, which contains at least some target complex, is then enriched (pulled down) using a solvent-containing composition, such as phosphate-buffered saline (PBS), and which preferably comprises an additional detectably double-labeled peptide sometimes called herein a detection-amplification peptide, to amplify the signal to some extent and add at least some additional sensitivity to the overall detection method. For example, the solid phase, which contains at least some of the target complex, is then enriched (pulled down) from the sample with either a centrifugation step or through the use of a magnet in the case of the solid phase being magnetic beads. Once the immobilized target complex is enriched from the sample, the interference contributed by the remaining sample can be removed using a standard micropipette. The immobilized target complex can then be washed using standard wash buffer, such as phosphate-buffered saline (PBS), to further remove contaminating or interfering substances present in the original sample. Then, the immobilized target complex, which contains both the target as well as the capture peptide, is resuspended into distilled water and/or PBS and the detection-amplification double-labeled peptide is added to increase the specificity of the overall detection method.

In some preferred embodiments, the sample is plasma or serum. The capture peptide is a biotin end-labeled prion probe:

(SEQ. ID. NO. 1)
Biotin-VVAGAAAAGAVHKMNTKPKMKHVAGAAAAGAVV

The solid phase is streptavadin-coated magnetic beads, which is effective to enrich the concentration of the peptide-misfolded protein complex in the sample. The detection-amplification peptide is labeled with pyrene on both ends:

Pyrene-VVAGAAAAGAVHKMNTKPKMKHVAGAAAAGAVV-Pyrene (SEQ. ID. NO. 2)

Extrinsic fluors such as pyrene allow detection of conformational changes using common fluorescence detection techniques. Optionally, an extra lysine residue is present at one end of the peptide to increase the effectiveness of the pyrene label:

Pyrene-VVAGAAAAGAVHKMNTKPKMKHVAGAAAAGAVVK-Pyrene (SEQ. ID. NO. 3)

Effective embodiments of the capture peptide for prions include at least the following sequences:

Biotin-KPKTNMKHVAGAAAAGAVV-OH (SEQ. ID. NO. 4)

Biotin-GGGKPKTNMKHVAGAAAAGAVV-OH (SEQ. ID. NO. 5)

Biotin-PPPKPKTNMKHVAGAAAAGAVV-OH (SEQ. ID. NO. 6)

Biotin-RRRKPKTNMKHVAGAAAAGAVV-OH (SEQ. ID. NO. 7)

Biotin-KKKKPKTNMKHVAGAAAAGAVV-OH (SEQ. ID. NO. 8)

H2N-KPKTNMKHVAGAAAAGAVV-Biotin (SEQ. ID. NO. 9)

H2N-KPKTNMKHVAGAAAAGAVVGGG-Biotin (SEQ. ID. NO. 10)

H2N-KPKTNMKHVAGAAAAGAVVPPP-Biotin (SEQ. ID. NO. 11)

H2N-KPKTNMKHVAGAAAAGAVVRRR-Biotin (SEQ. ID. NO. 12)

H2N-KPKTNMKHVAGAAAAGAVVKKK-Biotin (SEQ. ID. NO. 13)

Biotin-VVAGAAAAGAVHKMNTKPKMKHVAGAAAAGAVV-OH (SEQ. ID. NO. 14)

Biotin-GGGVVAGAAAAGAVHKMNTKPKMKHVAGAAAAGAVV-OH (SEQ. ID. NO. 15)

Biotin-PPPVVAGAAAAGAVHKMNTKPKMKHVAGAAAAGAVV-OH (SEQ. ID. NO. 16)

Biotin-RRRVVAGAAAAGAVHKMNTKPKMKHVAGAAAAGAVV-OH (SEQ. ID. NO. 17)

Biotin-KKKVVAGAAAAGAVHKMNTKPKMKHVAGAAAAGAVV-OH (SEQ. ID. NO. 18)

Biotin-DVVDAGAADAAGAVHKMNTKPKMKHVAGAADAAGADVVK-OH (SEQ. ID. NO. 19)

Biotin-KPKTNLKHVAGAAAAGAVV-OH (SEQ. ID. NO. 20)

Biotin-GGGKPKTNLKHVAGAAAAGAVV-OH (SEQ. ID. NO. 21)

Biotin-PPPKPKTNLKHVAGAAAAGAVV-OH (SEQ. ID. NO. 22)

Biotin-RRRKPKTNLKHVAGAAAAGAVV-OH (SEQ. ID. NO. 23)

Biotin-KKKKPKTNLKHVAGAAAAGAVV-OH (SEQ. ID. NO. 24)

H2N-KPKTNLKHVAGAAAAGAVV-Biotin (SEQ. ID. NO. 25)

H2N-KPKTNLKHVAGAAAAGAVVGGG-Biotin (SEQ. ID. NO. 26)

H$_2$N-KPKTNLKHVAGAAAAGAVVPPP-Biotin (SEQ. ID. NO. 27)

H$_2$N-KPKTNLKHVAGAAAAGAVVRRR-Biotin (SEQ. ID. NO. 28)

H$_2$N-KPKTNLKHVAGAAAAGAVVKKK-Biotin (SEQ. ID. NO. 29)

Biotin-VVAGAAAAGAVHKLNTKPKLKHVAGAAAAGAVV-OH (SEQ. ID. NO. 30)

Biotin-GGGVVAGAAAAGAVHKLNTKPKLKHVAGAAAAGAVV-OH (SEQ. ID. NO. 31)

Biotin-PPPVVAGAAAAGAVHKLNTKPKLKHVAGAAAAGAVV-OH (SEQ. ID. NO. 32)

Biotin-RRRVVAGAAAAGAVHKLNTKPKLKHVAGAAAAGAVV-OH (SEQ. ID. NO. 33)

Biotin-KKKVVAGAAAAGAVHKLNTKPKLKHVAGAAAAGAVV-OH (SEQ. ID. NO. 34)

Biotin-DVVDAGAADAAGAVHKLNTKPKLKHVAGAADAAGADVVK-OH (SEQ. ID. NO. 35)

Effective embodiments of the detection-amplification peptide for prions include at least the following sequences:

Pyr-DVVDAGAADAAGAVHKMNTKPKMKHVAGAADAAGADVV-Pyr (SEQ. ID. NO. 36)

Pyr-VVAGAAAAGAVHKMNTKPKMKHVAGAAAAGAVV-Pyr (SEQ. ID. NO. 37)

Pyr-DVVDAGAADAAGAVHKLNTKPKLKHVAGAADAAGADVV-Pyr (SEQ. ID. NO. 38)

Pyr-VVAGAAAAGAVHKLNTKPKLKHVAGAAAAGAVV-Pyr (SEQ. ID. NO. 39)

Pyr-DVVDAGAADAAGAVHKMNTKPKMKHVAGAADAAGADVVK-Pyr (SEQ. ID. NO. 40)

Pyr-VVAGAAAAGAVHKMNTKPKMKHVAGAAAAGAVVK-Pyr (SEQ. ID. NO. 41)

Pyr-DVVDAGAADAAGAVHKLNTKPKLKHVAGAADAAGADVVK-Pyr (SEQ. ID. NO. 42)

Pyr-VVAGAAAAGAVHKLNTKPKLKHVAGAAAAGAVVK-Pyr (SEQ. ID. NO. 43)

where Pyr is pyrene.

When the target protein is A Beta, effective embodiments of the capture peptide include at least the following sequences:

Biotin-KLVFFAEDVGSNKGAIIGLMK-OH (SEQ. ID. NO. 44)

Biotin-GGGKLVFFAEDVGSNKGAIIGLMK-OH (SEQ. ID. NO. 45)

-continued

Biotin-PPPKLVFFAEDVGSNKGAIIGLMK-OH (SEQ. ID. NO. 46)

Biotin-RRRKLVFFAEDVGSNKGAIIGLMK-OH (SEQ. ID. NO. 47)

Biotin-KKKKLVFFAEDVGSNKGAIIGLMK-OH (SEQ. ID. NO. 48)

$H_2N$-KLVFFAEDVGSNKGAIIGLMKGGG-Biotin (SEQ. ID. NO. 49)

$H_2N$-KLVFFAEDVGSNKGAIIGLMKPPP-Biotin (SEQ. ID. NO. 50)

$H_2N$-KLVFFAEDVGSNKGAIIGLMKRRR-Biotin (SEQ. ID. NO. 51)

$H_2N$-KLVFFAEDVGSNKGAIIGLMKKKK-Biotin (SEQ. ID. NO. 52)

While the embodiments described herein are preferable, other similarly effective embodiments exist for probe composition, label for the capture peptide, labels for the detection-amplification peptides, solid-phase composition and activity, and sample origin and type. It will be understood by those skilled in the art that a variety of labels and solid phases could be employed, depending on the specific analytical technique used. Analogs and derivatives of peptides can be effective.

Peptide derivatives can also include modifications to the native sequence, such as deletions, additions, and substitutions, provided the peptide substantially maintains the desired activity. These modifications may be deliberate, as through site-directed mutagenesis of the corresponding gene sequence, or may be accidental, such as through mutations of hosts that produce the proteins or errors due to PCR amplification. Furthermore, modifications may be made that have one or more of the following effects: reducing toxicity; increasing affinity and/or specificity for prions; facilitating cell processing; and facilitating presentation to B-cells and/or T-cells. Polypeptides described herein can be made in a variety of ways as in known in the art, including recombinant techniques, synthesis, purification from natural sources, or from tissue culture.

The capture peptides and detection-amplification peptides of the invention can be anywhere from about 10 to about 100 residues long, preferably from about 10 to 50 residues, more preferably from about 15 to about 45 residues. For example, they may be between 15 and 35 residues, 20 and 35 residues, 20 and 30 residues, 25 and 35 residues, 30 and 50 residues, any number or range of residues having at least 10 residues, and any number or range of residues having no more than 100 residues. One of ordinary skill in the art will understand that any specific residue length within these ranges is encompassed within the invention.

Analogs of the labels can also be used. To illustrate, the detection-amplification peptides can be doubly labeled with different fluorescent moieties than pyrene, such as pyrene butyrate, succinimidyl 1-pyrene, riboflavin, rosolic acid, 4-acetamido-4'-isothiocyanatostilbene-2,2'-disulfonic acid, acridine, 4-amino-N-[3-vinylsulfonyl)phenyl]naphth-alimide-3,5 disulfonate, anthranilamide, coumarin, cyanosine, 4',6-diaminidino-2-phenylindole (DAPI), diethylenetriamine pentaacetate, 4,4'-diisothiocyanatodi-hydro-stilbene-2,2'-disulfonic acid, eosin, eosin isothiocyanate, erythrosin, erythrosin B, isothiocyanate, ethidium, fluorescein, 5-carboxy-fluorescein (FAM), fluorescein, fluorescein isothiocyanate, fluorescamine, nitrotyrosine, pararosaniline, Phenol Red, B-phycoerythrin, or o-phthaldialdehyde. Preferred labels will form an excimeric state, enabling convenient signal detection.

In any of the methods using a solid phase described herein, the solid phase can be one or more of cellulose, modified cellulose, or another material derived from lignocellulosic biomass; polystyrene; polypropylene; polyethylene; polylactide; polyacrylamide; silicon; rubber; polysaccharides; latex; polyvinyl fluoride; nylon; polyvinylchloride; polycarbonate; starch; dextran; chitin; sand; silica; pumice; agarose; glass; metal; and any such materials in any form (such as particles, beads, planar surfaces, rods, and the like) and with any surface or bulk modification or activation such as one or more modifications selected from the group consisting of surface roughening, polarity induction, acid or base site generation, magnetic induction, thermal treatment, modification of hydrophobicity, and coating of various types. The solid phase can be particulate or can be in the form of a continuous surface and includes membranes, mesh, plates, pellets, slides, disks, capillaries, hollow fibers, needles, pins, chips, solid fibers, gels, and beads. A specific solid phase may include many elements as discussed herein, e.g. magnetically active beads coated with streptavadin or glass particles coated with a hydrophobic polymer.

The capture peptide is preferably labeled with biotin (single label on either end or both ends of the peptide) and the solid phase preferably comprises magnetic beads coated with streptavidin. The streptavidin is a preferred protein coating for the solid phase; yet one skilled in the art will recognize that it is not the only protein that could be utilized. For example, modifications could be made to streptavidin to alter its ligand-binding specificity, including its biotin-binding specificity, to be higher or lower for any certain ligand of interest. Biotin analogs that could be used include at least 2-iminobiotin and diaminobiotin.

Although the biotin-streptavidin binding pair is particularly effective, many other binding pairs are operative. To illustrate, but by no means to limit the scope of the invention, other suitable binding pairs include at least biotin-avadin, antigen-antibody, hapten-antibody, mimetope-antibody, receptor-hormone, receptor-ligand, agonist-antagonist, lectin-carbohydrate, enzyme-substrate or enzyme-substrate analog, and Protein A-antibody Fc.

For embodiments utilizing both a capture peptide and a detection-amplification peptide, the first and second peptides can be substantially the same or different. "Substantially the same" means that the first and second peptide reagents differ only in the inclusion of a detectable label in the second peptide reagent. The capture peptide and the detection-amplification peptide can be derived from peptide fragments from the same region of a prion or from peptide fragments from a different region of a prion. The first peptide reagent and the second peptide reagent can each be independently selected.

Any suitable means of detection can be used in this invention. In embodiments comprising assays involving the use of labeled peptides, detectable labels suitable for use in the invention include any molecule capable of detection, including radioactive isotopes, fluorescers, chemiluminescers, chromophores, fluorescent semiconductor nanocrystals, enzymes, enzyme substrates, enzyme cofactors, enzyme inhibitors, chromophores, dyes, metal ions, metal sols, ligands (e.g., biotin, strepavidin or haptens) and the like. Additional labels include, but are not limited to, those that use fluorescence, including those substances or portions thereof that are capable of exhibiting fluorescence in the detectable range. Particular examples of labels that may be used in the invention include horse radish peroxidase (HRP), fluorescein, FITC, rhodamine, dansyl, umbelliferone, dimethyl acridinium ester (DMAE), Texas red, luminol, NADPH and β-galactosidase. In addition, the detectable label may include an oligonucleotide tag, which can be detected by any known method of nucleic acid detection including PCR, TMA, b-DNA, and NASBA.

The moiety or chemical entity may be complexed or covalently bonded at or near the amino or carboxy end of the peptide, which is preferably endcapped with a short, hydrophobic peptide sequence. In preferred aspects of the present invention, both the amino and carboxy ends of the probe peptides are endcapped with small hydrophobic peptides ranging in size from about 1 to about 5 amino acids. These may be natural or synthetic, but are preferably natural (i.e., derived from a β-sheet formation region of a target protein). The fluorophores are preferably attached at or near the amino and/or carboxy end of the probe (preferably both) and may be, for example, pyrene, tryptophan, fluorescein, or rhodamine. It is preferable that the fluorophores form excimers when in the correct geometric orientation.

An "excimer" is an adduct that is not necessarily covalent and that is formed between a molecular entity that has been excited by a photon and an identical unexcited molecular entity. The adduct is transient in nature and exists until it fluoresces by emission of a photon. It is possible to recognize an excimer (or the formation of an excimer) by the production of a new fluorescent band at a wavelength that is longer than that of the usual emission spectrum. An excimer can be distinguished from fluorescence-resonance energy transfer since the excitation spectrum is identical to that of the monomer. The formation of the excimer is dependent on the geometric alignment of the fluorophores and is heavily influenced by the distance between them.

Preferred conformational transition following interaction with an analyte target is achieved by measuring fluorescence spectra under conditions where excimer formation can be analyzed. Typically, using pyrene as an exemplary fluorophor, the excitation wavelength would be about 350 nm and the observation wavelength 365-600 nm. The normal emission of monomer pyrene following excitation (simple fluorescence) is recorded as the maximum wavelength between about 370-385 nm.

The methods of the invention can be qualitative, semi-quantitative, or quantitative. Where the methods are practiced semi-quantitatively or quantitatively, they can further comprise generating one or more standard curves of misfolded protein concentrations in the sample of interest, then comparing the results obtained from the test sample to the standard curve(s). One skilled in the art, by referring to the teachings herein and to standard experimental methodologies, will understand how to practice the invention essentially qualitatively, essentially quantitatively, or semi-quantitatively, depending on the needs of the assay for the particular sample of interest.

In other aspects of the invention, the detection methods may be used in connection with methods for diagnosing prion-related diseases in human or non-human animal subjects; ensuring a substantially $PrP^{Sc}$-free blood supply, blood-products supply, or food supply; analyzing organ and tissue samples for transplantation; and monitoring the decontamination of medical equipment. The method comprises the steps of detecting prions in samples of blood (e.g., whole blood, plasma, platelets or serum) from collected blood samples by any of the methods described herein; eliminating any sample in which pathogenic prions are detected; and combining samples where pathogenic prions are not detected to provide a blood supply substantially free of pathogenic prions. In embodiments, the method can omit the detection step, per se, by merely practicing the method by binding misfolded proteins with probe and removing the probe-protein complexes. As a general matter, the amount of protein removed can be expressed in may ways, such as by percent removal, log units removed, or relative amount removed (e.g., fold reduction). For example, when practiced on TSE proteins or particles, the method can achieve a certain log units of infectivity removed, such as at least or about 3 log units of infectivity removed, at least or about 2 log units of activity removed, or at least or about 1 log unit of infectivity removed. When practiced on spiked samples, the method preferably provides an at least 3 log unit reduction in infectivity. Alternatively, in endemic samples, the method preferably results in a sample having below 2 log units of infectivity, more preferably below 1 log unit of infectivity. Another way to express the amount of target material removed is by reference to a percent removal. In embodiments, the method can remove at least 25% of the target protein, at least 40% of the target protein, at least 50% of the target protein, at least 60% of the target protein, at least 65% of the target protein, at least 75% of the target protein, at least 80% of the target protein, at least 85% of the target protein, at least 90% of the target protein, at least 95% of the target protein, at least 98% of the target protein, or at least 99% or more of the target protein, such as at least 99.5%, 99.9%, and 99.99% of the target protein.

In other aspects, the invention includes methods of preparing a food supply that is substantially free of pathogenic prions, comprising the steps of detecting prions, using any of the methods of detection described herein, samples collected from live or dead organisms that will enter the food supply or samples collected from food intended to enter the food supply; identifying samples in which pathogenic prions are detected; and removing from the food supply any live or dead organism or food intended to enter the food supply, in samples from which pathogenic prions are detected. Such a food supply is substantially free of pathogenic prions.

In other aspects, the present invention provides a method for substantially removing pathogenic misfolded proteins and prions from a sample. This method comprises providing a capture peptide of the invention, a solid phase of the invention, and one or more detection-amplification peptides of the invention. A sample suspected of containing misfolded proteins or prions is incubated with a preferred peptide that gives a high capture rate, followed by contacting with a preferred solid phase for a period of time whereby the complex formed between the capture peptide and the misfolded protein or prion, if present, is enriched from the sample. This technique can be optimized to achieve a desired removal efficiency for the misfolded proteins or prions, wherein monitoring of the efficiency can be conveniently carried out by adding a preferred double-labeled peptide to the pull-down phase, such that an analytical technique will monitor decrease in concentration of misfolded proteins or prions over time.

In any of the methods described herein the sample can be a biological sample obtained or derived from a living or once-living organism, such as organs, whole blood, blood fractions, blood components, plasma, platelets, serum, cerebrospinal fluid (CSF), brain tissue, nervous system tissue, muscle tissue, bone marrow, urine, tears, non-nervous system tissue, organs, and/or biopsies or necropsies. In preferred embodiments, the biological sample comprises blood, blood fractions or blood components.

In another aspect, the present invention provides kits for performing the methods of the invention. In some embodiments, the kits are diagnostic kits for diagnosing the presence of at least one misfolded protein in a sample, and thus a disease or disorder associated with at least one misfolded protein. In other embodiments, the kits are detection kits for screening human medical products, such as blood, organs, or tissues, for the presence of misfolded proteins associated with a disease or disorder. In other embodiments, the kits are detection kits for screening animal products, such as blood, organs, tissues, or meat, for the presence of misfolded proteins associated with a disease or disorder. In yet other embodiments, the kits are detection kits for monitoring the progression of a disease or disorder associated with a misfolded protein.

In general, the kits of the invention comprise some or all of the components necessary to practice one or more embodiments of the invention. Thus, a kit of the invention can comprise at least one conformational probe, such as a capture peptide and/or detection-amplification peptide, that binds to a pre-defined misfolded protein. The probe(s) and other components can be provided in one or more suitable containers within the kit. The kit can also comprise some or all of the buffers, reagents, and supplies needed to incubate and/or separate probe(s) and sample(s) or probe-misfolded protein complexes. The kit can comprise sufficient components to perform the method of the invention a single time or multiple times.

The containers of the kits can be any material suitable for containing one or more substances of the invention, such as a vial or ampule. The containers can be fabricated from materials such as glass, plastic, metal, paper, or a paper product. In some embodiments, the container is a glass or plastic ampule or vial that can be sealed, such as by a stopper, a stopper and crimp seal, or a plastic or metal cap such as a screw cap. In general, the container and seal are made of materials that can be sterilized by heat (dry or wet), radiation, or exposure to chemicals.

In some embodiments, the container comprises a sufficient amount of peptides to perform at least one embodiment of at least one method according to the invention. Thus, the kits can be, among other things, diagnostic kits, separation kits, test kits, or control kits. In some embodiments, the container is provided as a component of a larger kit, which includes suitable packaging and, optionally, instructions and other information relating to use of the peptides. Often, the kits will comprise some or all of the supplies and reagents to perform one or more control reactions to ensure the kits are performing properly and to provide baseline results against which test samples can be compared.

In certain configurations of the kits, the kit comprises multiple containers, each of which may contain peptides (conformational probes, i.e. capture peptides, and/or detection-amplification peptides) and other substances that are useful for performing one or more embodiment of a method of the invention. In embodiments where the kit comprises additional components or substances, they may be contained in the same or one or more different containers as the peptides and/or compositions. Where the kit comprises multiple containers or one container and other components, the containers and components are said to be in packaged combination within the kit. Where multiple containers are present, each container may contain enough peptide for practice of a single method of the invention, such as diagnosing misfolded proteins in a sample.

The kits of the invention can comprise substances that are useful for study of peptides and misfolded proteins. Such studies can comprise experiments to detect and/or study various peptide characteristics, functions, and effectiveness; to calibrate instruments; to separate misfolded proteins from a sample; to study interactions between peptide and microparticles (of various phases and activities); to calibrate peptide size; to calibrate separation techniques; to examine the interactions of various ligands and proteins; and to study surface-mediated reactions.

In some embodiments, the container is provided as a component of the kit, which includes suitable packaging and, optionally, instructions and/or other information relating to use of the contents of the kit. Typically, the kit is fabricated from a sturdy material, such as cardboard or plastic, and can contain the instructions or other information printed directly on it. One of skill in the art will immediately appreciate that numerous different configurations of container sizes and contents are envisioned by this invention, and thus not all permutations need be specifically recited herein.

EXAMPLES

The invention will now be described further in the following examples, which are illustrative of preferred embodiments of the invention, and should not be considered as limiting the invention in any way.

Example 1

Detection of Prion Protein in Biological Sample

A conformational propagation assay for prion protein in a murine brain sample was performed essentially as described in Published U.S. Patent Application 2005/0026265 A1, and as depicted in FIG. 1. The assay was performed using the murine-specific pallindromic 33-mer probe depicted below (SEQ. ID. NO. 49), labeled at both ends with a pyrene label. Other probes for human/hamster and sheep/bovine prions are presented below as well, and can be used for detection of prions in those species.

```
H2N-VVAGAAAAGAVHKLNTKPKLKHVAGAAAAGAVV-COOH
   (murine sequence; SEQ. ID. NO. 53)

H2N-VVAGAAAAGAMHKMNTKPKMKHMAGAAAAGAVV-COOH
   (human/hamster sequence; SEQ. ID. NO. 54)

H2N-VVAGAAAAGAVHKMNTKPKMKHVAGAAAAGAVV-COOH
   (sheep/bovine sequence; SEQ. ID. NO. 55)
```

For improved labeling, the above sequences have been modified to contain an additional lysine (K) residue at the C-terminus (SEQ. ID. NOs. 56-58) to allow addition of a pyrene label.

```
                                    (SEQ. ID. NO. 56)
H2N-VVAGAAAAGAVHKLNTKPKLKHVAGAAAAGAVVK-COOH (SEQ. ID. NO. 57)
H2N-VVAGAAAAGAMHKMNTKPKMKHMAGAAAAGAVVK-COOH (SEQ. ID. NO. 58)
H2N-VVAGAAAAGAVHKMNTKPKMKHVAGAAAAGAVVK-COOH.
```

Example 2

Figure 2:
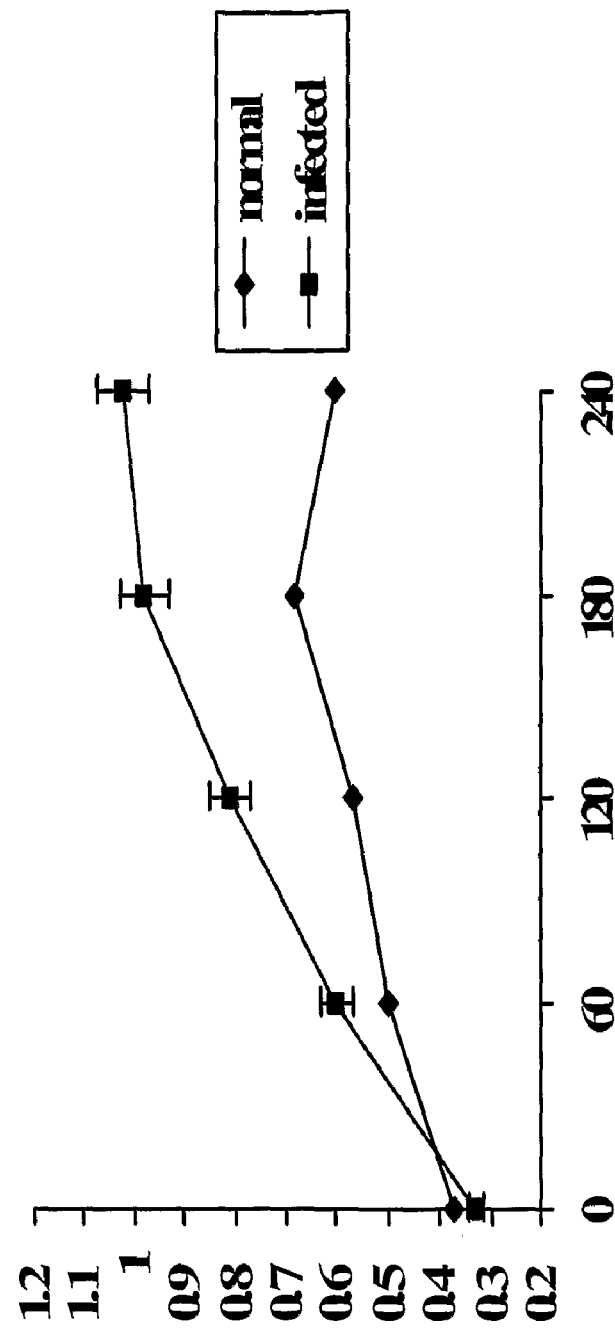
FIG. 2 depicts results of a standard catalytic-propagation assay used in the invention.
Figure 3:
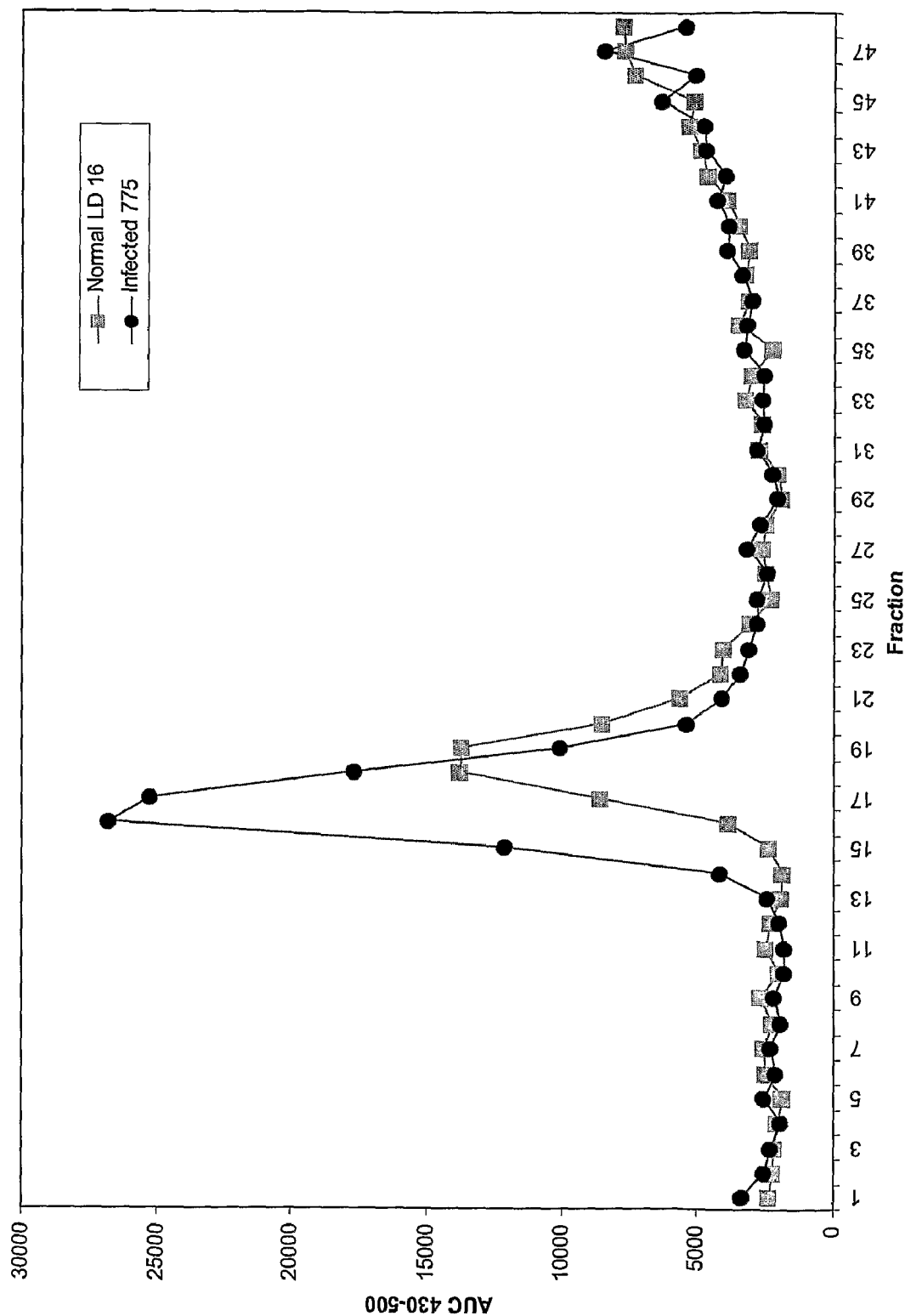
FIG. 3 depicts results of chromatographic separation of complexes of probe and misfolded-prion protein according to the method of the invention.
Figure 4:
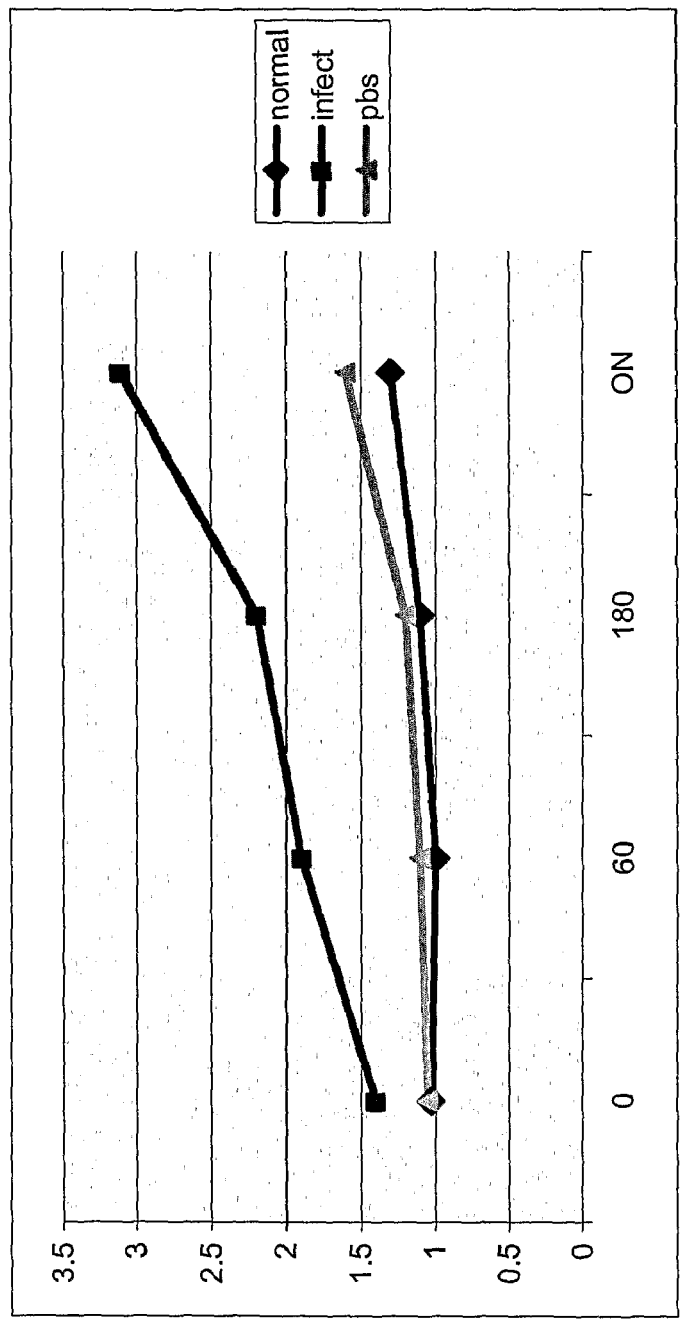
FIG. 4 depicts results of a standard catalytic-propagation assay for enriched sheep plasma, including PBS control, as practiced by the invention.
Figure 5:
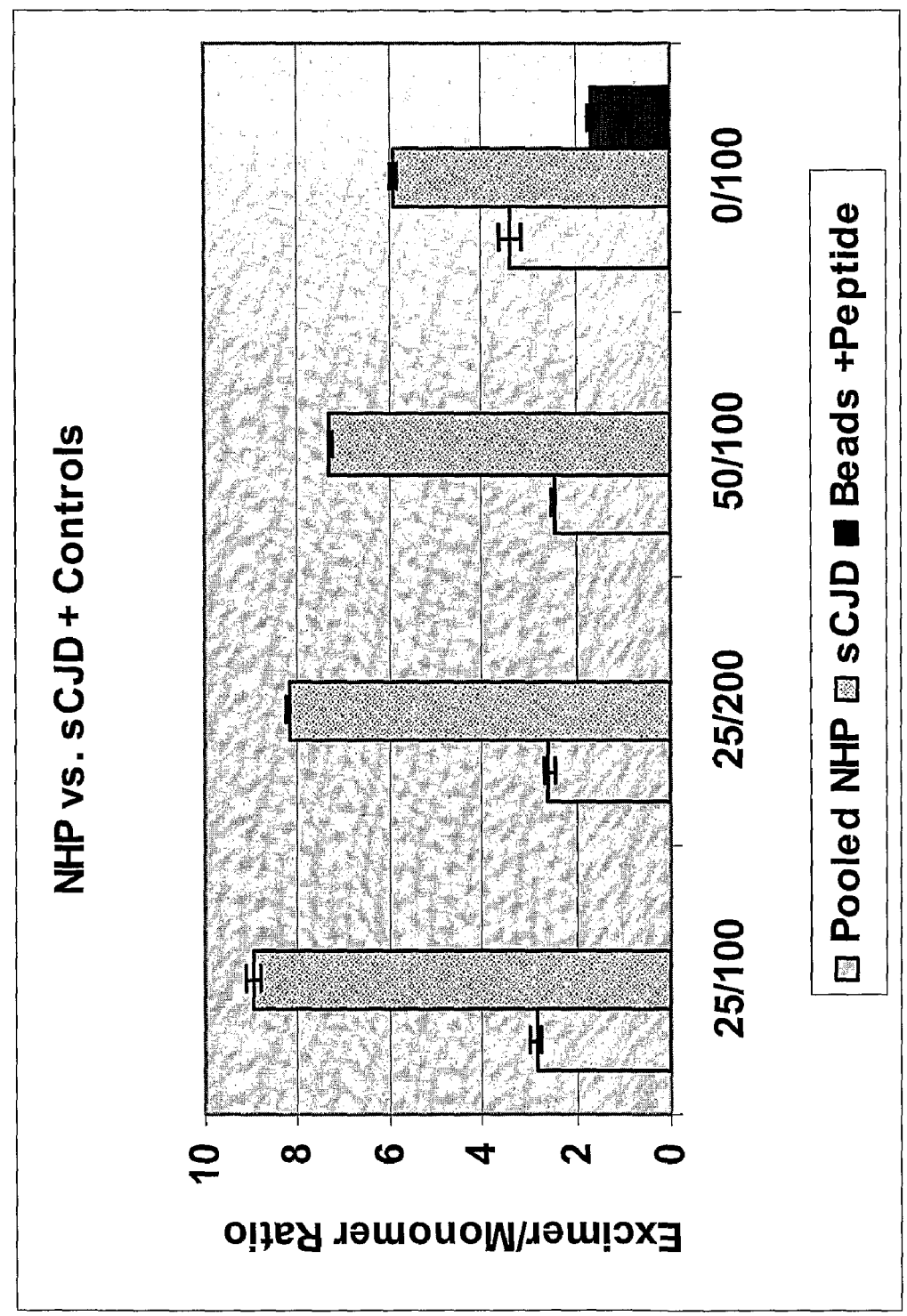
FIG. 5 depicts results of the selective-capture embodiment of the invention, with human plasma samples.
Figure 6:
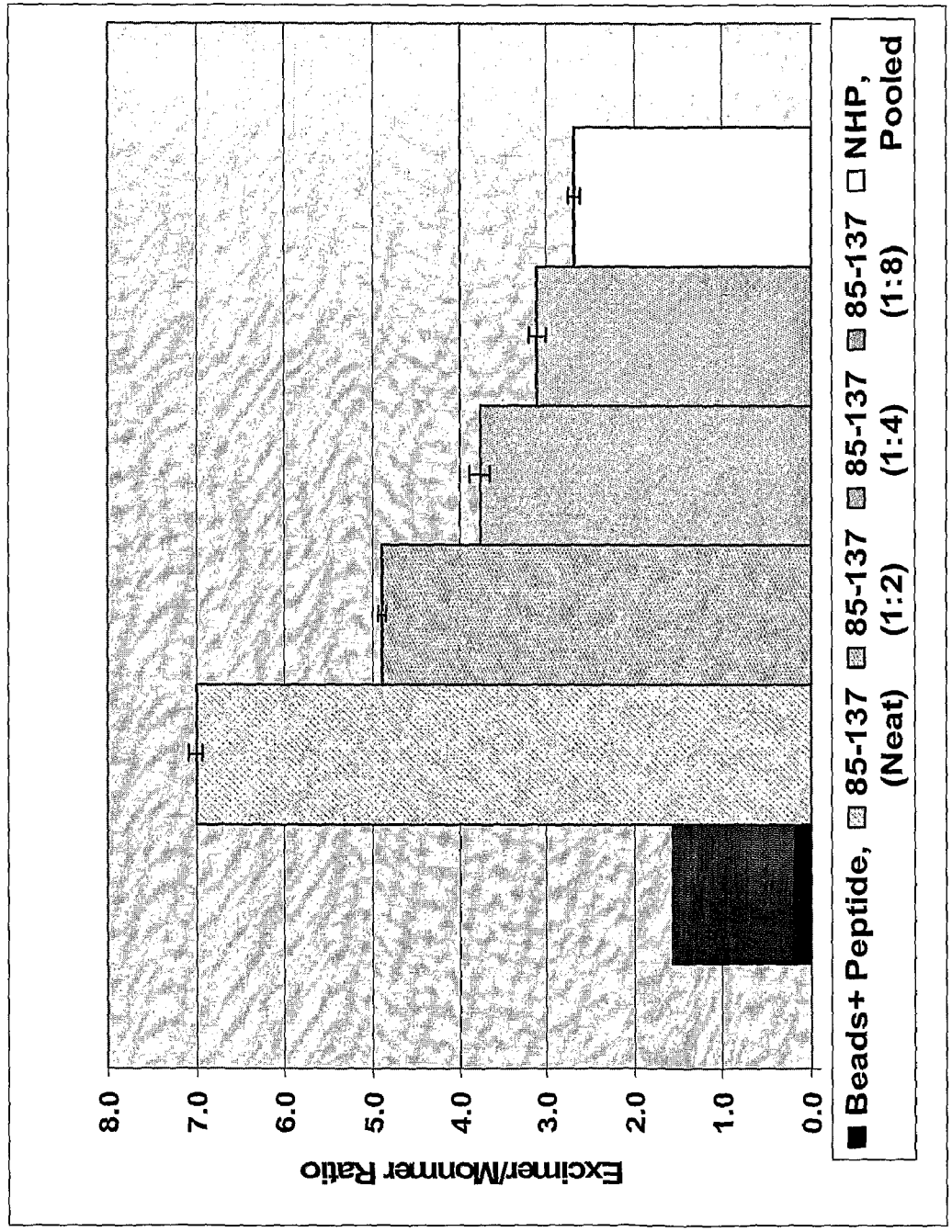
FIG. 6 depicts a protocol dose response for selective-capture misfolded-protein diagnostics (MPD).
Figure 7:
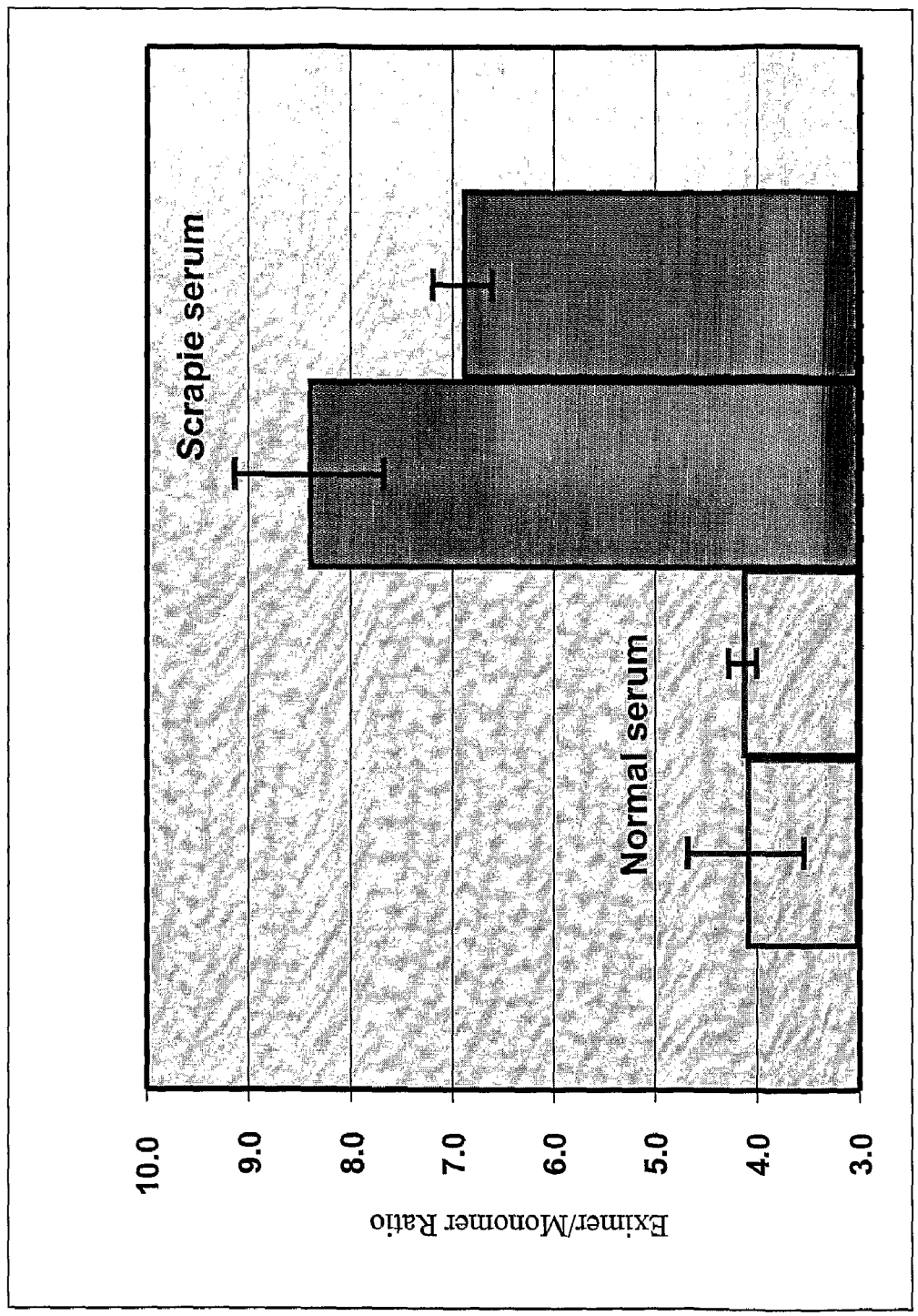
FIG. 7 depicts results of selective capture with sheep serum samples.
Figure 8A:
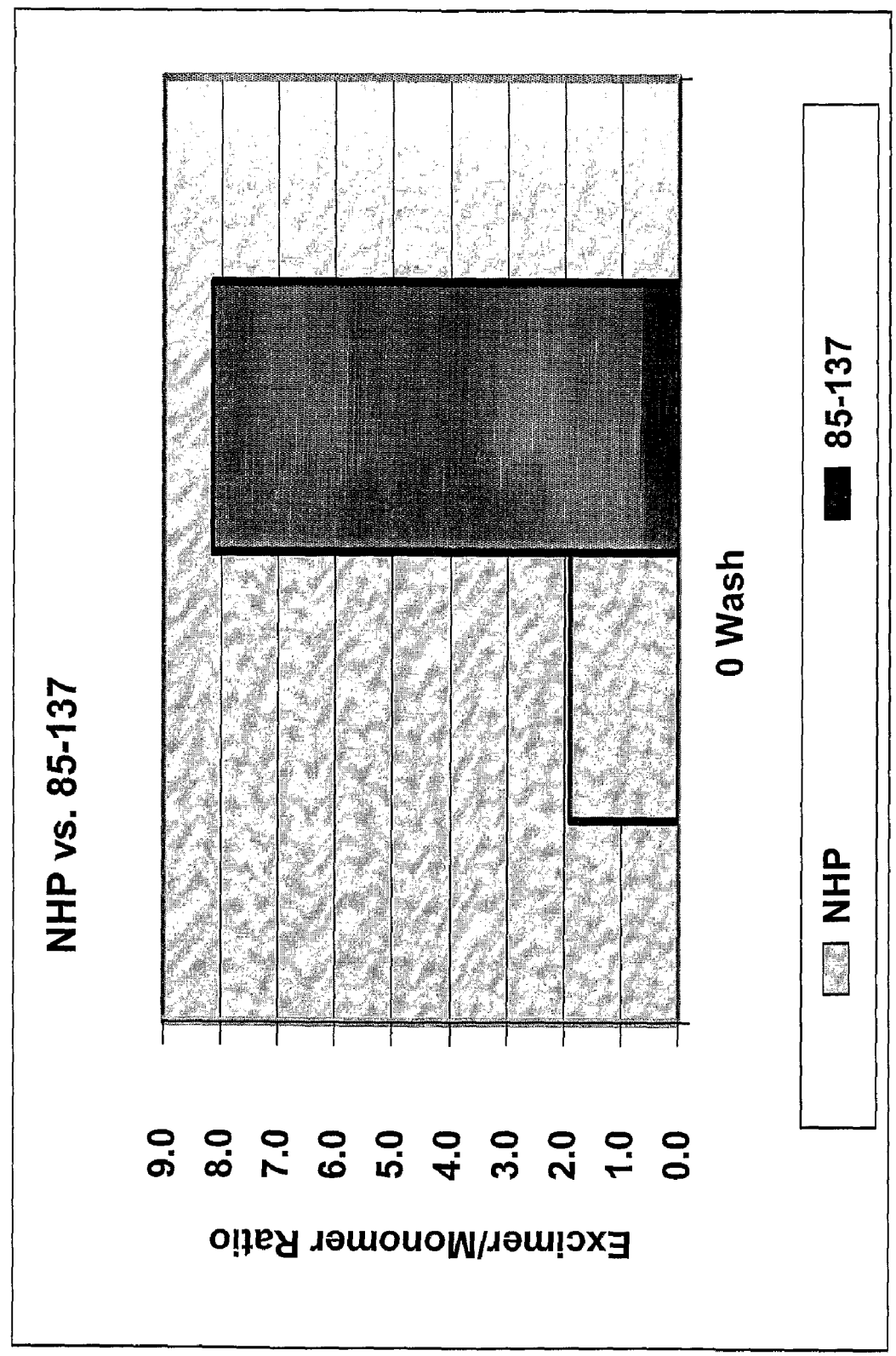
FIG. 8 depicts the effect of sequential washings of captured sCJD substrate from a solid phase comprising magnetic beads.
Figure 8B:
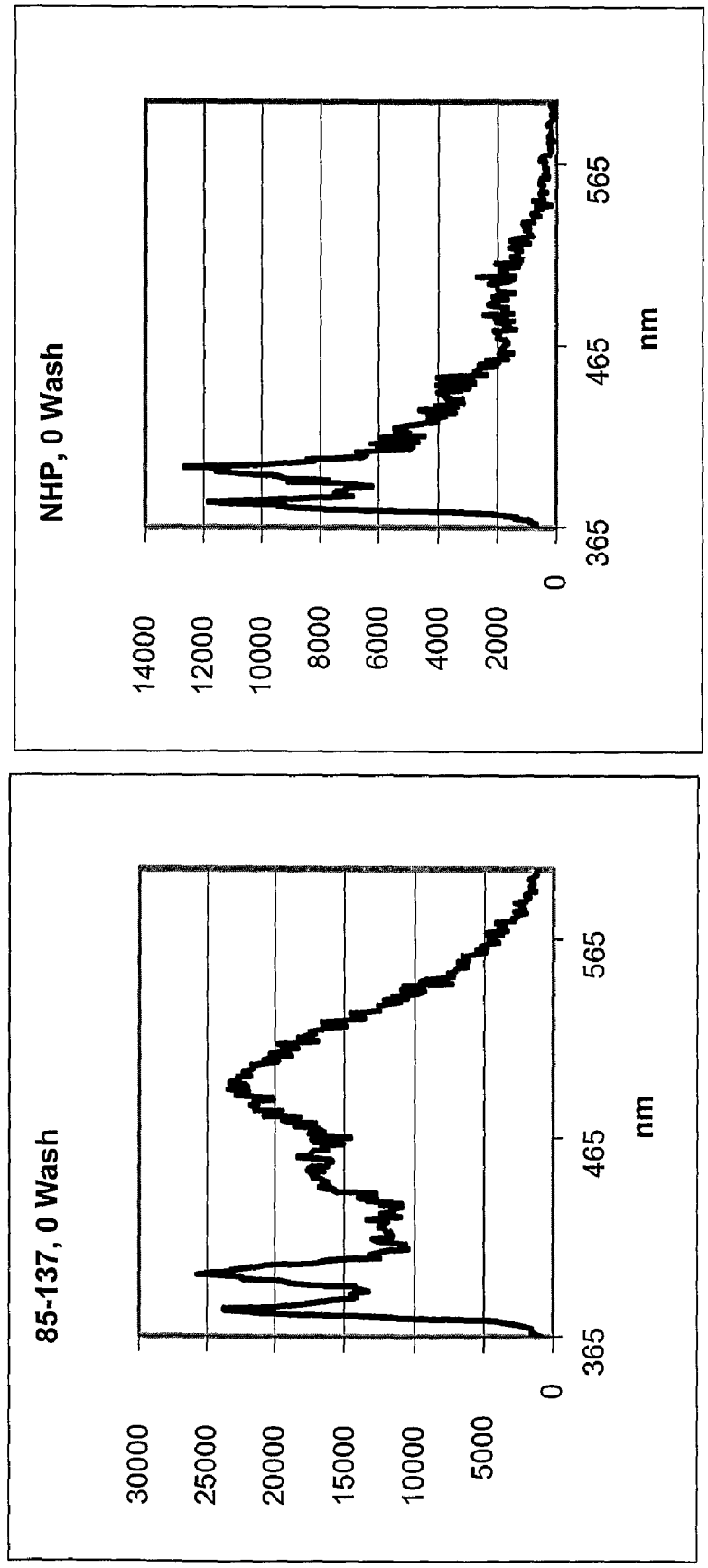
Figure 8C:
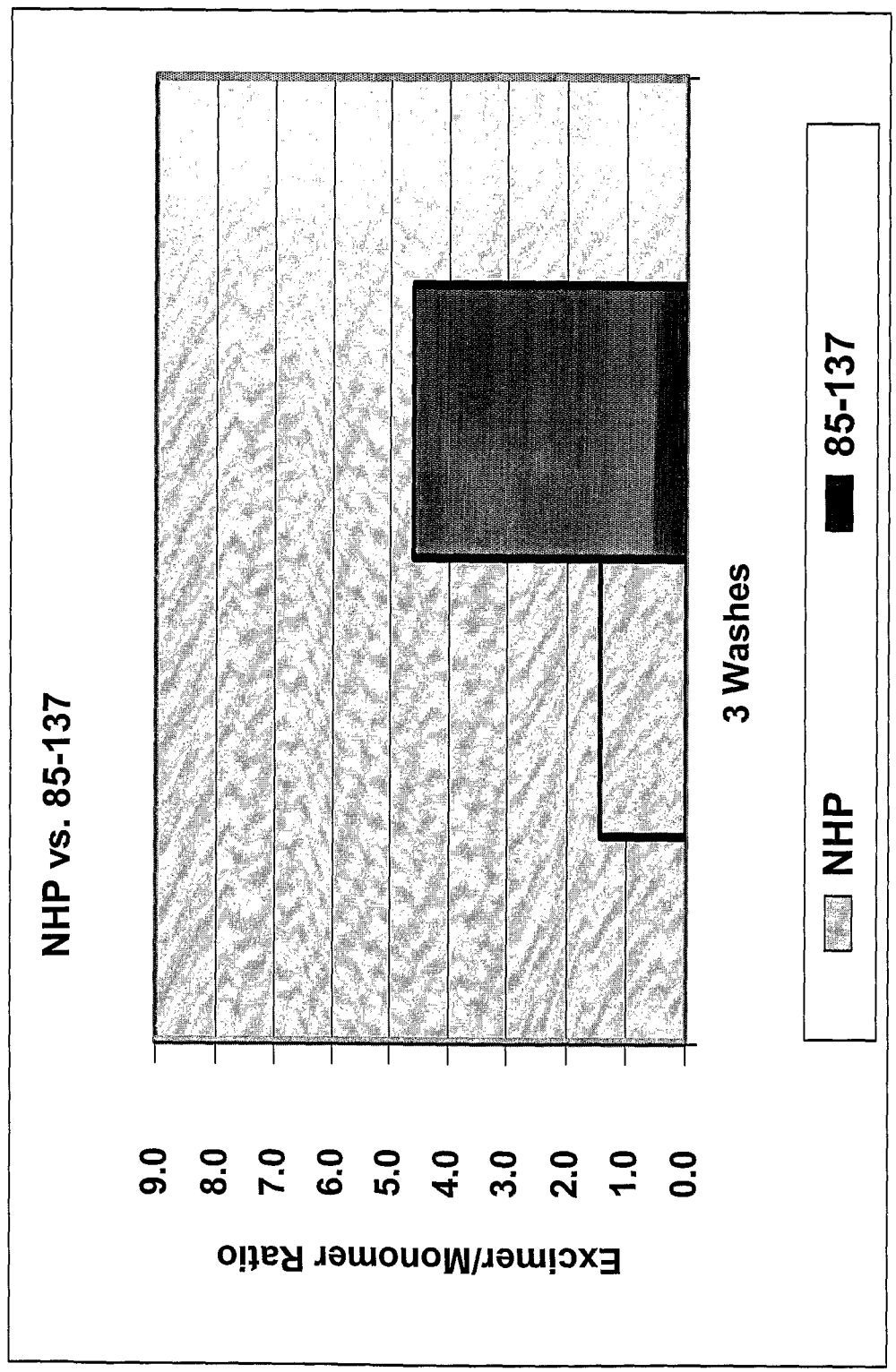
Figure 8D:
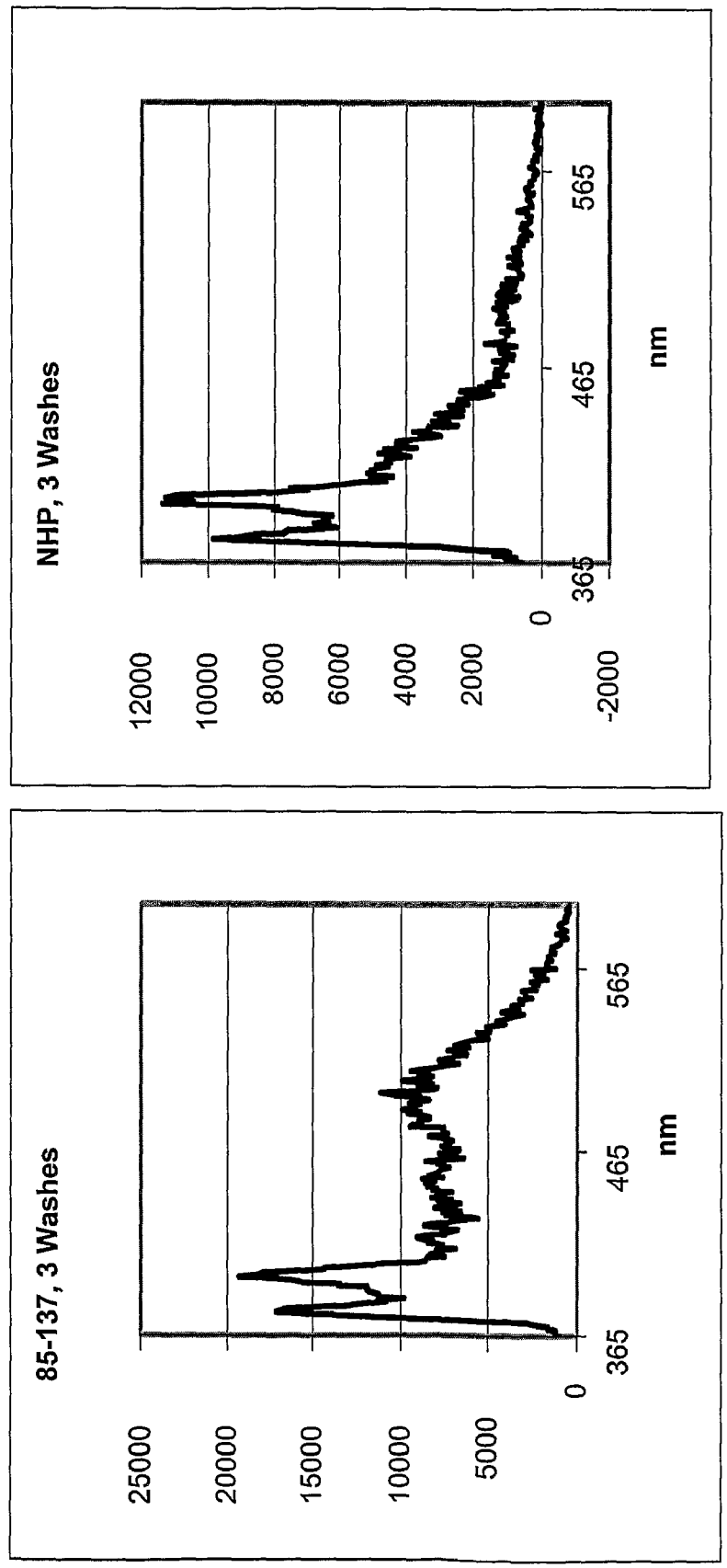
Figure 8E:
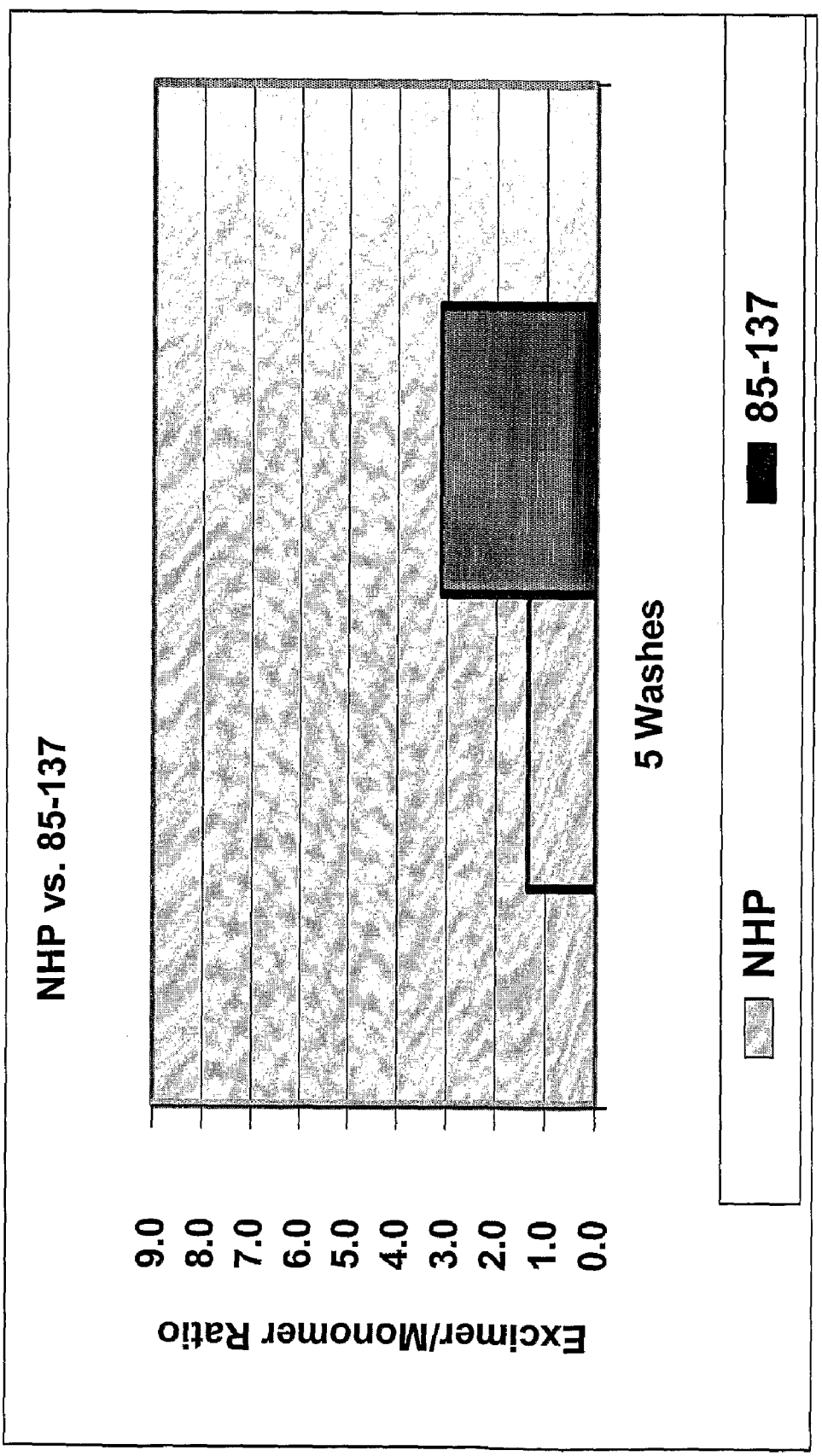
Figure 8F:
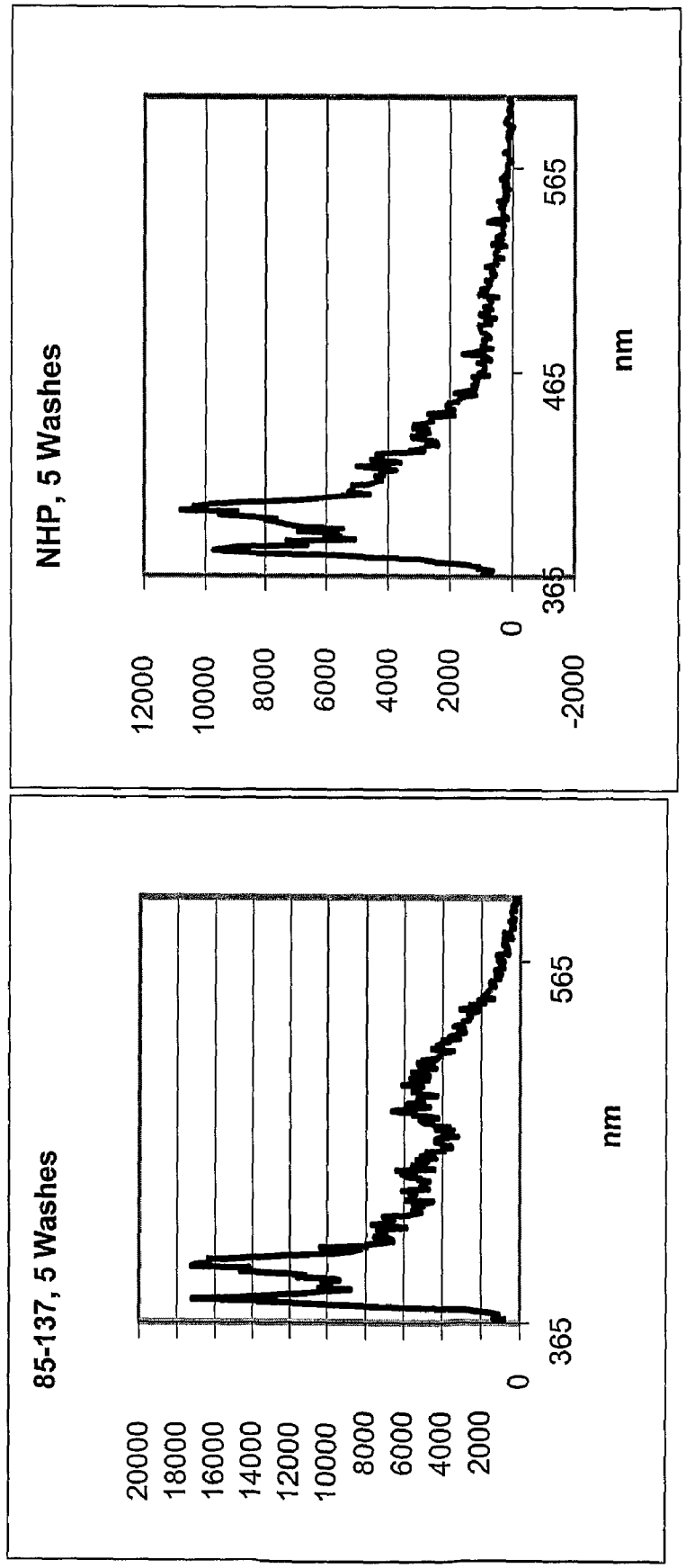

Demonstration of Kinetic Component of the Misfolded Protein Diagnostics (MPD) Assay Using Murine Brain Tissue Murine brain tissue from Scrapie-infected and healthy animals was obtained and fractionated on a sucrose gradient. The MPD Assay of Example 1 was performed, using phosphotungstic acid as a precipitating reagent, followed by addition of the murine specific peptide probe. The mixture was allowed to react in Tris:TFE (50:50) mixture per the time-course shown on the x-axis of FIG. 2. The results show suitable detection of prion protein in samples, which is above background levels for normal brain tissue.

Example 3

Fractionation of Prion-Containing Sample According to the Present Invention Sheep serum was obtained and mixed with sheep-specific peptide probe (see sequences above), and the mixture was incubated for a sufficient amount of time to permit association of the probe with any prion protein in the serum. The mixture was applied directly to a Sepharose 4B column, and fractions collected. The fractions were analyzed for fluorescence by exciting at 350 nm and scanning from 350-600 nm on a luminescent plate reader. The luminescence of each fraction from healthy and infected sera is depicted in FIG. 3. This data provides for visualization of elution of reactive fractions from the column. As can be seen, using the method of the present invention, not only can the infectious serum be distinguished from the healthy, it can occur in "real-time". Because the peptide was incubated with the sample prior to fractionation, the assay for misfolded protein is performed during the fractionation.

Example 4

MPD Assay of Non-fractionated Sheep Serum Samples

An MPD Assay was performed as follows. Normal and prion-infected sheep serum was obtained and applied directly to a Sepharose 4B column, and fractions collected. A solution of PBS was also run over a Sepharose 4B column for a negative control. In essence, this procedure was identical to that described in FIG. 3, with the exception that probe was not added to the serum before fractionating over the Sepharose 4B column.

Separately for each sample (infected, uninfected, PBS), fractions determined from Example 3 to contain the highest signal-to-noise ratio were combined with sheep-specific probe and evaluated. The fraction showing the highest ratio of excimer to monomer from the infected sample was chosen for the kinetic experimental data shown here. The identical fraction number for the healthy and PBS control were also chosen. For the timecourse (kinetic) experiment, sufficient time was provided for the probe to associate with any prion protein in the sample, using the typical 50:50 trifluoroethanol solvent conditions for the MPD Assay. The mixture was then assayed for fluorescence in a fluorescence scanning plate reader, and the data obtained is presented in FIG. 4. The data show that, in a similar fashion to the data shown in FIG. 2, the successful kinetics of the assay are apparent in fractionated sheep serum as well.

Example 5

Selective-Capture MPD with Human Plasma Samples 200 ul samples of human plasma, either sCJD or pooled normal, were incubated with biotin-labeled peptide overnight. Dynal magnetic beads, coated with streptavidin, were added at the ratio of biotin peptide to beads of 25:100, 25:200, 50:100, or 0:100. A magnet was used to remove the enriched target material from the plasma samples. After washing and resuspending, a double-labeled (pyrene) fluorophore peptide was added and after incubation, the emission scan captured. FIG. 5 shows the successful signal separation between the sCJD plasma sample and pooled normal human plasma (NHP).

Example 6

Selective-Capture MPD Assay Dose Response

The same protocol as in Example 5 was followed, except that the sCJD 85-137 sample was diluted into normal human plasma 1:2, 1:4, and 1:8 (FIG. 6). Dilution of neat human sCJD plasma into normal plasma resulted in a diminished fluorescence signal proportional and in a dose-response manner in the Selective Capture MPD Assay as expected. While the actual level of $PrP^{TSE}$ present in the starting sCJD 85-137 sample is not known, as a clinical specimen, the expected maximum level would be 20-30 IU/ml. Using this approximation, with a testing volume of 200 ul, the neat sample would have contained 4-6 IU, and the two-fold serial dilutions of 1:2, 1:4 and 1:8 would have contained 2-3, 1-1.5, and 0.5-0.75 IU, respectively. These results reflect a LOD (level of detection) near 1 IU.

Example 7

Selective-Capture MPD Protocol with Sheep Serum Samples

The same protocol as in Example 5 was followed, except that the samples tested were two different Scrapie sheep serum samples and two normal healthy sheep serum samples (FIG. 7). The Selective Capture MPD Protocol is successful for sheep serum samples. The signal-to-noise ratio is excellent between normal sheep serum and infected Scrapie ($PrP^{Sc}$ or $PrP^{TSE}$) sheep serum.

Example 8

Effect of Sequential Washings of Captured sCJD Substrate from Magnetic Beads

FIG. 8 shows direct evidence of binding of the $PrP^{TSE}$ (sCJD 85-137) substrate to the biotin-labeled capture peptide, and effective interaction with the solid phase (magnetic beads). Repeated washings in PBS causes the $PrP^{TSE}$ to dissociate. This experiment demonstrates that the interaction of the double-labeled fluorophore peptide is dependent upon what is associated with the "pull-down" material on the magnetic beads. The target ($PrP^{TSE}$) material is captured by the biotin-labeled peptide which itself associates with the streptavidin covering the surface of the magnetic beads. This material can be washed away with subsequent PBS washings. FIG. 8 demonstrates that as the number of washings increases, the signal associated with the excimeric peak, i.e. 430-530 nm, of the fluorophore-labeled detection peptide is strongly diminished for the sCJD sample but not for the pooled normal human plasma sample. Specifically, FIGS. 8A and 8B show the eximer to monomer ratios of the two samples (FIG. 8A) and fluorescence scans showing peak emission (FIG. 8B) of the two samples without washing, while FIGS. 8C and 8D show data from the same assays after washing of the samples 3 times, while FIGS. 8E and 8F show data from the same assays after washing of the samples 5 times.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:

1. A method for detecting the presence or amount of misfolded protein in a sample, said method comprising:
   (a) combining (i) a sample containing or suspected of containing a misfolded protein with (ii) a conformational capture peptide to make a mixture,
      wherein the conformational capture peptide preferentially interacts with the pathogenic, misfolded form of the misfolded protein and assumes a predominantly β-sheet conformation upon association with the misfolded protein,
   (b) incubating the mixture for an amount of time sufficient to form a complex comprising an association of at least one molecule of any misfolded protein present in the sample and at least one molecule of conformational capture peptide,
   (c) exposing the mixture to conditions that separate, at least partially, the complex, if present, from at least one other substance in the mixture, and
   (d) detecting the presence or absence of any association between the conformational capture peptide and any misfolded protein.

2. The method of claim 1, further comprising, after the exposing step and prior to the detecting step, adding at least one double-labeled peptide to the complex, if present.

3. The method of claim 1, wherein the incubating and exposing steps are carried out concurrently.

4. The method of claim 2, wherein at least one double-labeled peptide comprises an amino acid sequence selected from the group consisting of SEQ. ID. NOs. 2, 3 and 36-43.

5. The method of claim 1, wherein the misfolded protein is a prion protein.

6. The method of claim 5, wherein at least one conformational capture peptide comprises an amino acid sequence selected from the group consisting of SEQ. ID. NOs. 1, 4-35, and 53-58.

7. The method of claim 1, wherein the misfolded protein is an A Beta protein.

8. The method of claim 7, wherein at least one conformational capture peptide comprises an amino acid sequence selected from the group consisting of SEQ. ID. NOs. 44-52.

9. The method of claim 1, wherein the exposing step comprises binding the conformational capture probe, misfolded protein, or complex thereof to a solid phase.

10. The method of claim 9, wherein the solid phase is modified to increase the desired separation during the exposing step, by a means selected from the group consisting of surface roughening, polarity induction, acid or base site generation, magnetic induction, thermal treatment, modification of hydrophobicity, and placement of a chemical or biologically active coating onto the solid surface.

11. The method of claim 10, wherein the solid phase comprises magnetic beads coated with streptavidin.

12. The method of claim 11, wherein at least one conformational capture peptide comprises biotin or a biotin analog.

13. The method of claim 1, wherein the presence of an association between the conformational capture peptide and misfolded protein is used to diagnose a disease associated with the misfolded protein.

14. The method of claim 1, wherein the sample is an animal product.

15. The method of claim 1, wherein the sample is selected from the group consisting of human blood products, human tissues, and human organs.

16. The method of claim 1, further comprising monitoring the removal of pathogenic misfolded proteins at least at one point in time.

17. The method of claim 1, wherein the exposing step results in the removal, from the mixture, of at least 25% of the pathogenic misfolded proteins present in the sample.

18. The method of claim 1, wherein the exposing step results in the removal, from the mixture, of at least 50% of the pathogenic misfolded proteins present in the sample.

19. The method of claim 1, wherein the exposing step results in the removal, from the mixture, of substantially all of the pathogenic misfolded proteins present in the sample.

20. The method of claim 1, wherein at least one conformational capture peptide is labeled with a detectable label.

21. The method of claim 20, wherein at least one conformational capture peptide is labeled with a detectable label at each end of the peptide.

22. The method of claim 2, wherein the double-labeled peptide preferentially interacts with the pathogenic, misfolded form of the misfolded protein and assumes a predominantly β-sheet conformation upon association with the misfolded protein.

23. The method of claim 2, wherein the amino acid sequence of the conformational capture peptide is substantially the same as the amino acid sequence of the double-labeled peptide.

24. The method of claim 2, wherein the amino acid sequence of the conformational capture peptide is different from the amino acid sequence of the double-labeled peptide.

25. The method of claim 1, wherein at least one conformational capture peptide comprises a moiety selected from the group consisting of radioactive isotopes, fluorescers, chemiluminescers, chromophores, fluorescent semiconductor nanocrystals, enzymes, enzyme substrates, enzyme cofactors, enzyme inhibitors, dyes, metal ions, metal sols and ligands.

26. The method of claim 25, wherein at least one conformational capture peptide comprises a moiety selected from the group consisting of pyrene butyrate, succinimidyl 1-pyrene, riboflavin, rosolic acid, 4-acetamido-4'-isothiocyanatostilbene-2,2'-disulfonic acid, acridine, 4-amino-N-[3-vinylsulfonyl)phenyl]naphthalimide-3,5 disulfonate, anthranilamide, coumarin, cyanosine, 4',6-diaminidino-2-phenylindole (DAPI), diethylenetriamine pentaacetate, 4,4'-diisothiocyanatodi-hydro-stilbene-2,2'-disulfonic acid, eosin, eosin isothiocyanate, erythrosin, erythrosin B, isothiocyanate, ethidium, fluorescein, 5-carboxyfluorescein (FAM), fluorescein, fluorescein isothiocyanate, fluorescamine, nitrotyrosine, pararosanilme, Phenol Red, B-phycoerythrin, or o-phthaldialdehyde.

27. The method of claim 2, wherein at least one conformational capture peptide or at least one double-labeled peptide comprises a moiety selected from the group consisting of radioactive isotopes, fluorescers, chemiluminescers, chromophores, fluorescent semiconductor nanocrystals, enzymes, enzyme substrates, enzyme cofactors, enzyme inhibitors, dyes, metal ions, metal sols and ligands.

28. The method of claim 27, wherein at least one double-labeled peptide comprises a moiety selected from the group consisting of pyrene butyrate, succinimidyl 1-pyrene, riboflavin, rosolic acid, 4-acetamido-4'-isothiocyanatostilbene-2,2'-disulfonic acid, acridine, 4-amino-N-[3-vinylsulfonyl)phenyl]naphthalimide-3,5 disulfonate, anthranilamide, coumarin, cyanosine, 4',6-diaminidino-2-phenylindole (DAPI), diethylenetriamine pentaacetate, 4,4'-diisothiocyanatodi-hydro-stilbene-2,2'-disulfonic acid, eosin, eosin isothiocyanate, erythrosin, erythrosin B, isothiocyanate, ethidium, fluorescein, 5-carboxyfluorescein (FAM), fluorescein, fluorescein isothiocyanate, fluorescamine, nitrotyrosine, pararosanilme, Phenol Red, B-phycoerythrin, or o-phthaldialdehyde.

29. The method of claim 1, wherein the exposing step comprises using size-exclusion chromatography or filtration.

30. The method of claim 9, wherein the solid phase comprises one or more materials selected from the group consisting of cellulose, modified cellulose, lignocellulosic biomass, polystyrene, polypropylene, polyethylene, polylactide, polyacrylamide, silicon, rubber, polysaccharides, latex, polyvinyl fluoride, nylon, polyvinylchloride, polycarbonate, starch, dextran, chitin, sand, silica, pumice, agarose, glass, and metal.

31. The method of claim 1, wherein the sample is a biological sample obtained from a living or once-living organism.

32. The method of claim 31, wherein the biological sample is selected from the group consisting of organs, whole blood, blood fractions, blood components, plasma, platelets, serum, cerebrospinal fluid, brain tissue, nervous system tissue, muscle tissue, bone marrow, urine, and tears.

* * * * *

UNITED STATES PATENT AND TRADEMARK OFFICE
CERTIFICATE OF CORRECTION

| | | |
|---|---|---|
| PATENT NO. | : 8,372,593 B2 | Page 1 of 1 |
| APPLICATION NO. | : 11/884316 | |
| DATED | : February 12, 2013 | |
| INVENTOR(S) | : Orser et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1525 days.

Signed and Sealed this
Eighteenth Day of November, 2014

Michelle K. Lee
*Deputy Director of the United States Patent and Trademark Office*